US010457648B2

(12) United States Patent
Gosselin et al.

(10) Patent No.: US 10,457,648 B2
(45) Date of Patent: Oct. 29, 2019

(54) PROCESS FOR PREPARING (CYCLOPENTYL[D]PYRIMIDIN-4-YL)PIPERAZINE COMPOUNDS

(71) Applicants: F. HOFFMANN-LA ROCHE AG, Basel (CH); GENENTECH, INC., South San Francisco, CA (US)

(72) Inventors: Francis Gosselin, South San Francisco, CA (US); Chong Han, South San Francisco, CA (US); Hans Iding, Basel (CH); Reinhard Reents, Basel, CA (US); Scott Savage, South San Francisco, CA (US); Beat Wirz, Basel (CH)

(73) Assignees: GENENTECH INC., South San Francisco, CA (US); F. HOFFMANN-LA ROCHE AG, Basel (CH)

( * ) Notice: Subject to any disclaimer, the term of this patent is extended or adjusted under 35 U.S.C. 154(b) by 0 days.

(21) Appl. No.: 15/514,188

(22) PCT Filed: Sep. 25, 2015

(86) PCT No.: PCT/US2015/052143
§ 371 (c)(1),
(2) Date: Mar. 24, 2017

(87) PCT Pub. No.: WO2016/049414
PCT Pub. Date: Mar. 31, 2016

(65) Prior Publication Data
US 2017/0247338 A1    Aug. 31, 2017

Related U.S. Application Data

(60) Provisional application No. 62/055,893, filed on Sep. 26, 2014.

(51) Int. Cl.
| | | |
|---|---|---|
| C07D 239/70 | (2006.01) |
| C07D 239/54 | (2006.01) |
| C07D 239/42 | (2006.01) |
| C07C 253/30 | (2006.01) |
| C07C 255/22 | (2006.01) |
| C07B 57/00 | (2006.01) |
| C12P 41/00 | (2006.01) |
| C07C 253/34 | (2006.01) |
| C12N 9/78 | (2006.01) |

(52) U.S. Cl.
CPC ............ *C07D 239/70* (2013.01); *C07B 57/00* (2013.01); *C07C 253/30* (2013.01); *C07C 253/34* (2013.01); *C07C 255/22* (2013.01); *C07D 239/42* (2013.01); *C07D 239/54* (2013.01); *C12N 9/78* (2013.01); *C12P 41/00* (2013.01); *C12Y 305/05001* (2013.01); *C07B 2200/07* (2013.01)

(58) Field of Classification Search
CPC .. C07D 239/70; C07D 239/54; C07D 239/42; C07C 253/34; C07C 255/22; C12N 9/78; C12P 41/00; C12Y 305/05001; C07B 57/00
See application file for complete search history.

(56) References Cited

U.S. PATENT DOCUMENTS

| | | | |
|---|---|---|---|
| 8,063,050 B2 | 11/2011 | Mitchell et al. |
| 8,853,199 B2 | 10/2014 | Mitchell et al. |
| 9,278,917 B2 | 3/2016 | Remarchuk et al. |
| 9,309,204 B2 | 4/2016 | Lane et al. |
| 9,315,471 B2 | 4/2016 | Babu et al. |
| 9,359,340 B2 | 6/2016 | Mitchell et al. |
| 9,416,110 B2 | 8/2016 | Askin et al. |
| 9,676,730 B2 | 6/2017 | Askin et al. |
| 9,790,190 B2 | 10/2017 | Lane et al. |
| 9,862,689 B2 | 1/2018 | Iding et al. |
| 2016/0235754 A1 | 8/2016 | Mitchell et al. |
| 2016/0297773 A1 | 10/2016 | Iding et al. |
| 2018/0169099 A1 | 6/2018 | Mitchell et al. |
| 2018/0258054 A1 | 9/2018 | Askin et al. |

FOREIGN PATENT DOCUMENTS

| | | |
|---|---|---|
| EP | 0667343 A1 | 9/1995 |
| WO | 2006052546 A2 | 5/2006 |
| WO | 2008006040 A1 | 1/2008 |
| WO | 2013068785 A1 | 5/2013 |
| WO | 2013173736 A1 | 11/2013 |
| WO | 2013173768 A1 | 11/2013 |
| WO | 2013173779 A1 | 11/2013 |
| WO | 2013173784 A1 | 11/2013 |
| WO | 2016049414 | * 3/2016 |

OTHER PUBLICATIONS

Gimbert, et al., "Michael additions catalyzed by phosphines. An overlooked synthetic method", Tetrahedron 61, 8598-8605.
Krasovskiy, et al., "A LiCl-Mediated Br/Mg Exchange Reaction for the Preparation of Functionalized Aryl- and Heteroarylmagnesium Compounds from Organic Bromides", Angew. Chem. Int. Ed., 43, 3333-3336 (2004).
O'Hara, "Synergistic effects in the activation of small molecules by s-block elements", Organomet. Chem. 37, 1-26 ( 2011).
Patent Cooperation Treaty, International Searching Authority, Search Report and Written Opinion for PCT/US2015/052143, 11 pages dated Nov. 23, 2015.
Caruso, T , et al., "Electrochemically Induced Addition Reactions in the Absence of Solvent and Supporting Electrolyte", Advanced Synthesis & Catalysis 348(14), 1942-1947 (2006).
Han, C , et al., "Asymmetric Synthesis of Akt Kinase Inhibitor Ipatasertib", Organic Letters 19(18), 4806-4809 (2017).
Palombi, L , et al., "An innovative strategy for electrochemically-promoted addition reactions", Chemical Communications 16, 1846-1847 (2004).

* cited by examiner

*Primary Examiner* — Alexander R Pagano
*Assistant Examiner* — Ebenezer O Sackey

(57) ABSTRACT

The present disclosure relates to processes for preparing (cyclopentyl[d]pyrimidin-4-yl)piperazine compounds, and more particularly relates to processes for preparing (R)-4-(5-methyl-7-oxo-6,7-dihydro-5H-cyclopenta[d] pyrimidin-4-yl)piperazine and N-protected derivatives thereof, which may be used as an intermediate in the synthesis of Ipatasertib (i.e., (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)-propan-1-one). The present disclosure additionally relates to various compounds that are intermediates employed in these processes.

14 Claims, No Drawings

PROCESS FOR PREPARING (CYCLOPENTYL[D]PYRIMIDIN-4-YL)PIPERAZINE COMPOUNDS

PRIORITY OF INVENTION

This application claims priority from U.S. Provisional Application No. 62/055,893, filed 26 Sep. 2014. The entire content of this provisional application is hereby incorporated herein by reference.

FIELD OF THE DISCLOSURE

The present disclosure relates to processes for preparing (cyclopentyl[d]pyrimidin-4-yl)piperazine compounds, and more particularly relates to processes for preparing (R)-4-(5-methyl-7-oxo-6,7-dihydro-5H-cyclopenta[d]pyrimidin-4-yl)piperazine and N-protected derivatives thereof, which may be used as an intermediate in the synthesis of Ipatasertib (i.e., (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)-propan-1-one). The present disclosure additionally relates to various compounds that are intermediates employed in these processes.

BACKGROUND OF THE DISCLOSURE

AKT (also known as Protein Kinase B) is a serine/threonine protein kinase that is overexpressed in certain human tumors. Ipatasertib is an AKT inhibitor that is currently being evaluated in clinical trials for the treatment of solid tumors, gastric cancer, and prostate cancer. Ipatasertib is disclosed in, for example, U.S. Pat. No. 8,063,050 (see, e.g., Example 14), as well as International Patent Application Publication No. WO 2008/006040.

(R)-4-(5-methyl-7-oxo-6,7-dihydro-5H-cyclopenta[d]pyrimidin-4-yl) piperazine, or the N-protected derivative thereof, may be used as an intermediate in the synthesis of Ipatasertib. Processes for preparing this intermediate are reported in, for example, International Patent Application Publication No. WO 2013/173736 and International Patent Application Publication No. WO 2013/173768. Scheme 1 of WO 2013/173768 is shown below:

Scheme 1

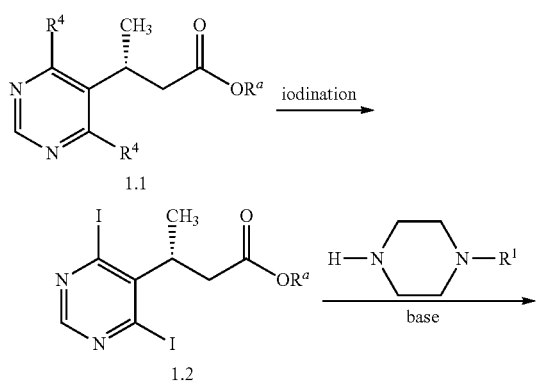

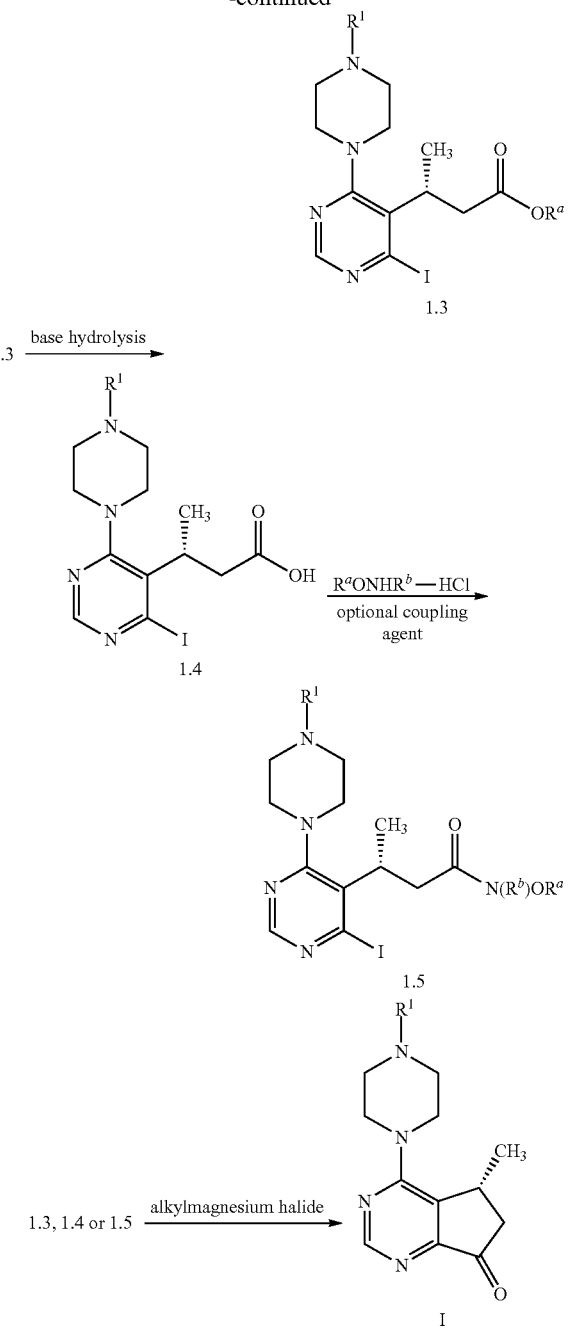

The present disclosure provides improved processes for the large-scale manufacturing of (cyclopentyl[d]pyrimidin-4-yl)piperazine compounds, and more particularly (R)-(5-methyl-7-oxo-6,7-dihydro-5H-cyclopenta[d]pyrimidin-4-yl)piperazine, as well as N-protected derivatives thereof. As compared to currently known processes, the processes of the present disclosure advantageously provide improvements in, for example, process conditions, reagent selection, complexity of required unit operations, scalability, and the like.

SUMMARY OF THE DISCLOSURE

The present disclosure provides improved processes for preparing (cyclopentyl[d]pyrimidin-4-yl)piperazine compounds, and more particularly (R)-4-(5-methyl-7-oxo-6,7- dihydro-5H-cyclopenta[d]pyrimidin-4-yl)piperazine, as well as N-protected derivatives thereof, such as for example tert-butyl-(R)-4-(5-methyl-7-oxo-6,7-dihydro-5H-cyclopenta[d]pyrimidin-4-yl)piperazine-1-carboxylate. The present disclosure further provides processes for preparing AKT inhibitors, and in particular Ipatasertib, using such improved processes for preparing these (cyclopentyl[d]pyrimidin-4-yl)piperazine compounds and N-protected derivatives thereof.

In one embodiment, the present disclosure is directed to a process for preparing a compound of Formula I:

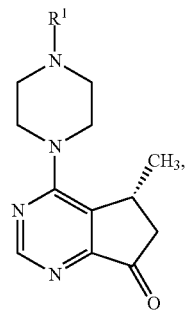

Formula I or a salt thereof, the process comprising contacting a compound of Formula III:

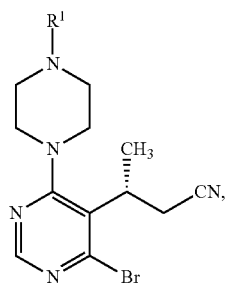

Formula III or a salt thereof, with a metalating agent to form the compound of Formula I, or a salt thereof, wherein Fe is hydrogen or an amino protecting group.

In this or another embodiment, the present disclosure is further directed to such a process, wherein the compound of Formula III, or a salt thereof, is prepared by contacting a compound of Formula IV:

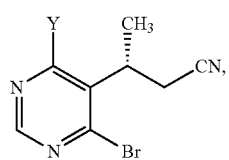

Formula IV or salt thereof, wherein Y is selected from chloro and bromo, with a piperazine compound having the structure:

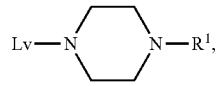

or salt thereof, wherein Lv is a leaving group and $R^1$ is an amino protecting group.

In this or yet another embodiment, the present disclosure is still further directed to such a process, wherein the compound of Formula IV, or a salt thereof, is prepared by brominating a compound of Formula V:

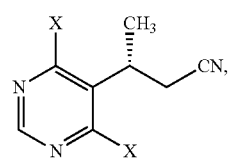

Formula V or salt thereof; wherein each X is independently selected from chloro and hydroxyl. In one particular embodiment, the present disclosure is directed to such a process wherein the compound or salt of Formula IV is not isolated after the bromination of the compound or salt of Formula V and prior to reaction with the piperazine compound, as detailed above.

In this or yet another embodiment, the present disclosure is still further directed to such a process, wherein the compound or salt of Formula IV (wherein Y is Br) is prepared by brominating a compound of Formula $V_b$:

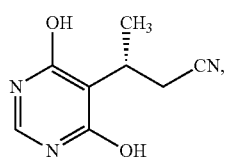

Formula $V_b$ or a salt thereof, to form the compound or salt of Formula IV. Alternatively, the compound or salt of Formula IV (wherein Y is Cl, or more particularly Br) is prepared by chlorinating the compound of Formula $V_b$, or a salt thereof, to form a compound of Formula $V_c$:

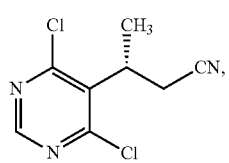

Formula $V_c$ or a salt thereof; and, brominating the compound or salt of Formula $V_c$ to form the compound of Formula IV, or salt thereof. In one particular embodiment, the present disclosure is directed to such a process wherein the compound or salt of Formula $V_c$ is not isolated after the chlorination of the compound or salt of Formula $V_b$ and prior to bromination.

In this or yet another embodiment, the present disclosure is still further directed to such a process wherein the compound or salt of Formula $V_c$ is not isolated after the chlorination of the compound or salt of Formula $V_b$ and prior to bromination to form the compound or salt of Formula IV, and further that the compound or salt of Formula IV is not isolated after the bromination of the compound or salt of Formula $V_c$ and prior to reaction with the piperazine compound to form the compound or salt of Formula III.

In this or yet another embodiment, the compound or salt of Formula $V_b$ is prepared by cyclizing a compound of $VI_b$:

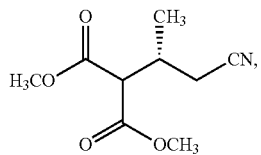

Formula $VI_b$ or a salt thereof.

In this or yet another embodiment, the compound of Formula $IV_b$, or a salt thereof, is prepared by (i) contacting crotononitrile with malonate to form an isomeric mixture comprising a compound of Formula $VI_a$ and the compound of Formula $VI_b$:

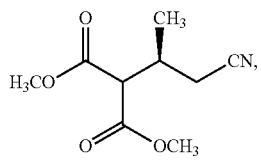

Formula $VI_a$ or salts thereof, and then (ii) separating the compound or salt of Formula $VI_b$ from the compound or salt of Formula $VI_a$ in the isomeric mixture. In one particular embodiment, the compound of Formula $VI_b$, or salt thereof, is separated from the isomeric mixture by enzymatic resolution. In this or another particular embodiment, the isomeric mixture is not isolated from a reaction production mixture resulting from contacting crotononitrile with malonate, prior to separation of the compound of Formula $VI_b$, or salt thereof; that is, the compound of Formula $VI_b$, or salt thereof, is separated directly from the reaction product mixture.

In yet another embodiment, the present disclosure is still further directed to a process for preparing a compound of Formula IX:

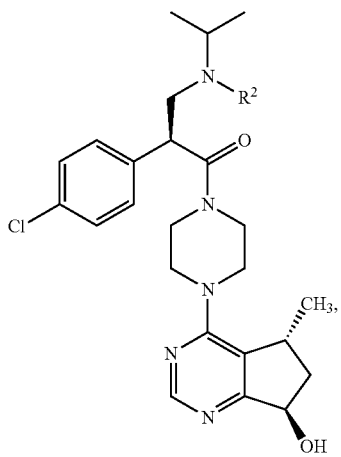

Formula IX or a salt thereof, wherein $R^2$ is hydrogen or an amino protecting group, the process comprising: (i) contacting a compound of Formula III,

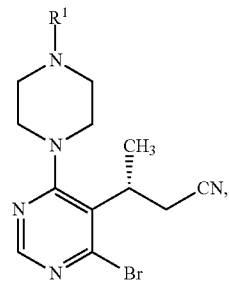

Formula III or a salt thereof, wherein $R^1$ is hydrogen or an amino protecting group, with a metalating agent to form a compound of Formula I:

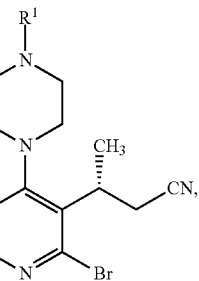

Formula I or salt thereof; (ii) reducing the compound of Formula I, or a salt thereof, to form a compound of Formula $VII_a$:

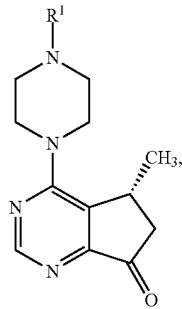

Formula $VII_a$ or salt thereof; (iii) optionally deprotecting the compound of Formula $VII_a$, or salt thereof, to form a compound of Formula $VII_b$:

Formula $VII_b$ or salt thereof; and (iv) contacting the compound of Formula VII$_b$, or salt thereof, with a compound of Formula VIII:

Formula VIII

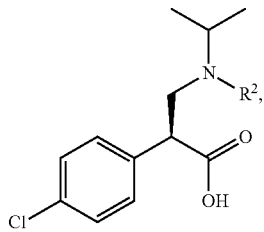

or salt thereof, to form the compound of Formula IX, or salt thereof.

In yet another embodiment, the present disclosure is still further directed to a compound of Formula V$_b$:

Formula V$_b$

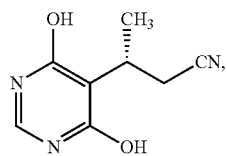

or salt thereof.

In yet another embodiment, the present disclosure is still further directed to a compound of Formula V$_c$:

Formula V$_c$

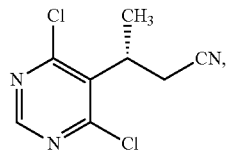

or salt thereof.

In yet another embodiment, the present disclosure is still further directed to a compound of Formula IV$_b$:

Formula IV$_b$

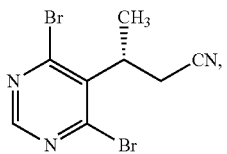

or salt thereof.

In yet another embodiment, the present disclosure is still further directed to a compound of Formula IV$_c$:

Formula IV$_c$

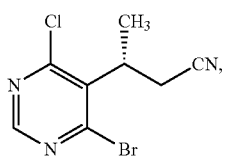

or salts thereof.

In yet another embodiment, the present disclosure is still further directed to a compound of Formula III:

Formula III

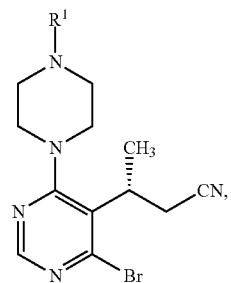

or salt thereof, wherein $R^1$ is hydrogen or an amino protecting group.

Optional modifications for one or more of the above embodiments, as well as additional details related thereto, are further provided herein below.

DETAILED DESCRIPTION OF THE DISCLOSURE

As further detailed herein below, the present disclosure is generally directed to an improved process for preparing (cyclopentyl[d]pyrimidin-4-yl)piperazine compounds, and more particularly is directed to improved processes for preparing (R)-4-(5-methyl-7-oxo-6,7-dihydro-5H-cyclopenta[d]pyrimidin-4-yl)piperazine, as well as N-protected derivatives thereof, such as for example tert-butyl-(R)-4-(5-methyl-7-oxo-6,7-dihydro-5H-cyclopenta[d]pyrimidin-4-yl)piperazine-1-carboxylate, as generally illustrated in Scheme 2, below:

Scheme 2

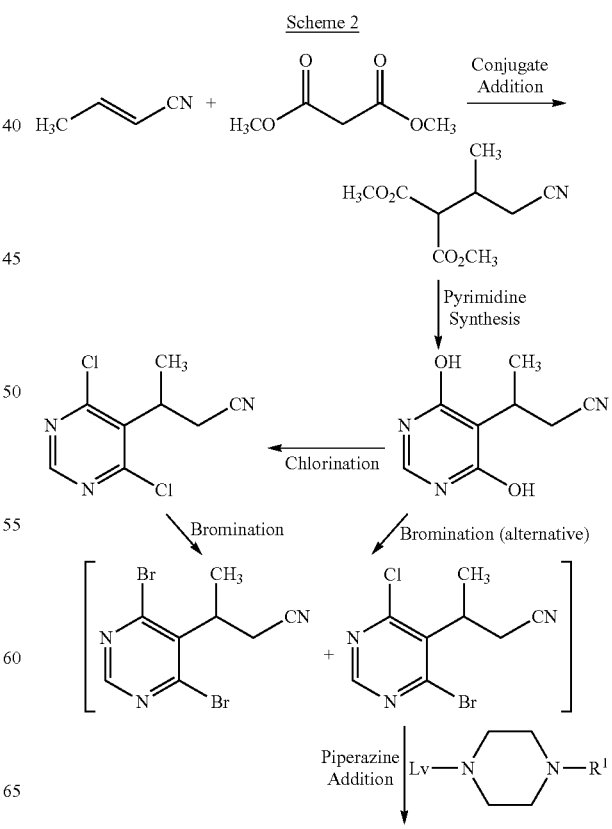

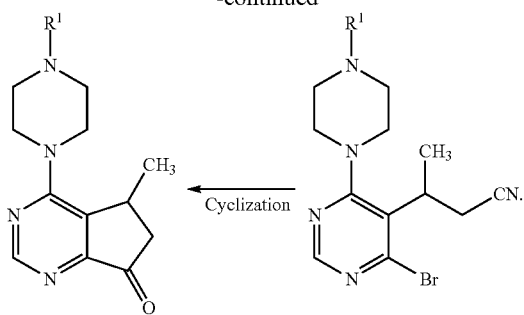

With respect to Scheme 2, it is to be noted that the dihydroxy-nitrile pyrimidine may be directly brominated, or alternatively may be first chlorinated, the resulting chlorinated reaction product being subsequently brominated.

It is to be further noted, with respect to Scheme 2, that one or more of the compounds illustrated therein may be prepared and/or utilized in a particular isomer or stereochemical configuration, or alternatively may be prepared and/or utilized as a racemate or a mixture of stereoisomers. In one particular embodiment, however, the R-isomer of one or more of the reaction products is prepared or isolated using means generally known in the art and/or as further detailed herein, and optionally further used in any subsequent reaction step. For example, enzymatic resolution may be used to preferentially obtain the R-isomer of the conjugate addition reaction product (compound of Formula VI$_b$), the R-isomer then being used in subsequent reaction steps, as further illustrated in Scheme 3, below:

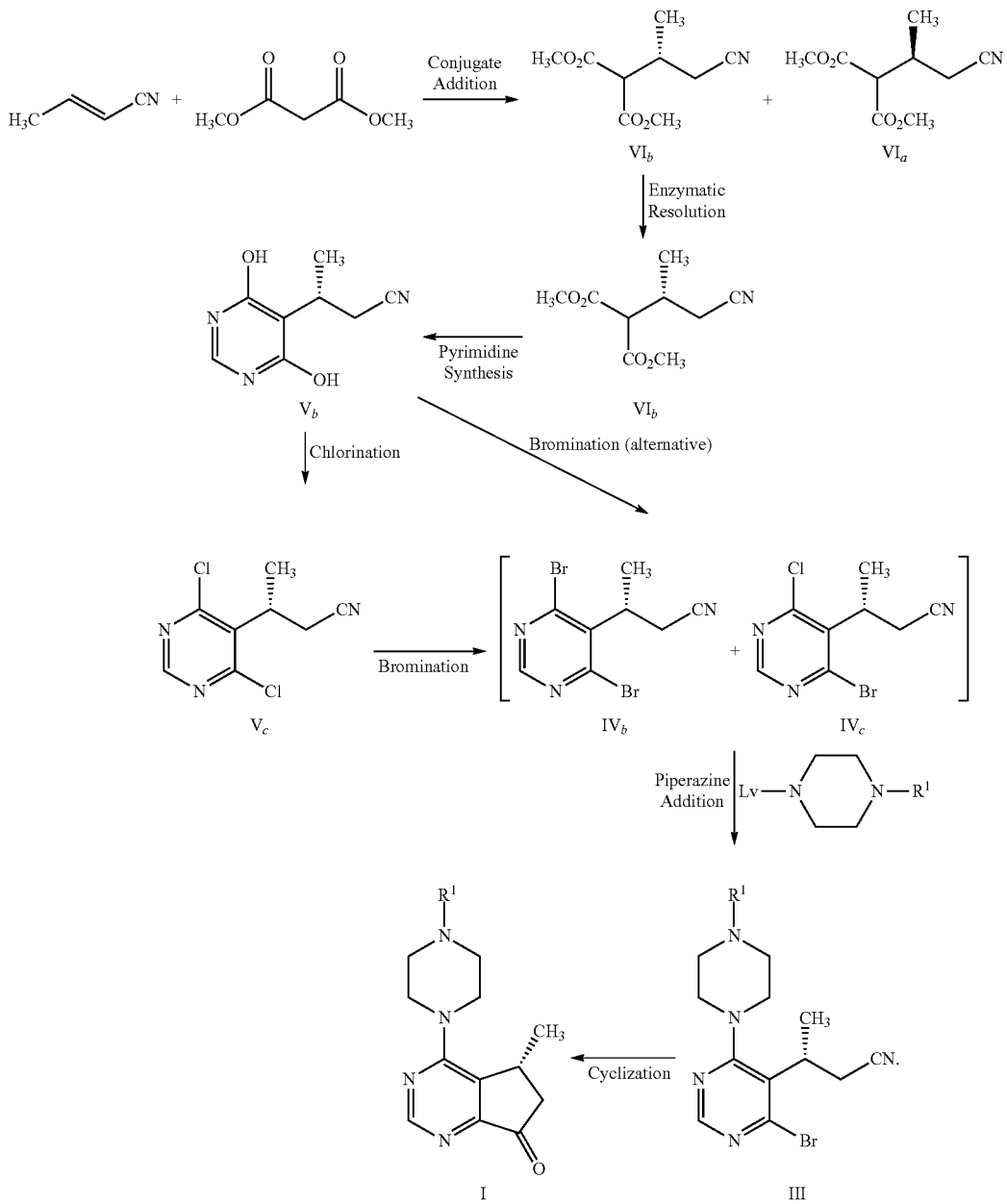

Advantageously, the present process eliminates the need for an iodination step and/or the use of an iodide-containing reagent therein, thus being more cost-effective and environmentally-friendly than other processes which utilize them. In particular, the present process involves a cyclization or ring closure reaction step to form the cyclopentyl ring of the compound of Formula I that utilizes a bromo-nitrile substituted compound of Formula III, rather than for example an iodo-ester, an iodo-acid or an iodo-amide substituted analogue compound. As further illustrated by the comparative results provided herein below (see, e.g., Example 6), experience to-date suggests that the cyclization or ring closure reaction is less effective when the chloro-nitrile substituted analogue compound is used.

The present process further allows for (i) a more reactive or stronger brominating agent, and/or (ii) more harsh or a broader range of halogenation reaction conditions (e.g., higher reaction temperatures), to be used to carry out the bromination step, due to the presence of the nitrile moiety in, for example, the compounds of Formula $V_b$ and Formula $V_c$. In contrast, use of such a brominating agent and/or such harsh reaction conditions to prepare a bromo-ester substituted analog compound results in ester-cleavage and concomitant lactone formation.

The present process is still further advantageous, inasmuch as proper selection of the brominating agent used in the bromination reaction step results in the formation of volatile byproducts that can be removed by distillation. In this regard, it is generally believed that removal of these byproducts from the mixture, as the reaction is carried out, enables the reaction equilibrium to be better controlled, such that the reaction favors bromine exchange at both locations; that is, in for example Scheme 3 above, both chlorine atoms in the compound of Formula $V_c$, or hydroxyl moieties in the compound of Formula $V_b$, are replaced by bromine. Such a process enables greater conversion to the desired reaction product (i.e., the compound of Formula $IV_b$), and reduces the amount of impurities that would otherwise be present in the reaction mixture.

The present process is still further advantageous, inasmuch as bromination of the nitrile-substituted compound of Formula $V_c$ enables fewer equivalents of the brominating agent to be used in comparison, for example, to equivalents of an iodinating agent, in an iodination reaction of an ester-substituted analogue compound as illustrated in Scheme 1 above (e.g., iodination of Compound 1.1 to Compound 1.2).

The present process is still further advantageous, inasmuch as reaction of the bromo-nitrile substituted compounds of Formula $IV_b$ and Formula $IV_c$ with the piperazine compound may be carried out at lower temperatures, and in particular at about room temperature, as compared, for example, to reaction of the iodo-ester substituted analogue compounds with the piperazine compound as illustrated in Scheme 1 above (e.g., Compound 1.2 to Compound 1.3), which is typically carried out at 60° C. Lower reaction temperatures advantageously allow for the conservation of energy, and/or reduce the potential of unwanted byproduct formation.

The present process is still further advantageous, inasmuch as it enables one or more of the reaction steps to be carried out in a through-process manner, thus eliminating the need for isolation of an intermediate reaction product before one or more subsequent reaction steps are carried out. In particular, (i) the reaction product of the bromination step (i.e., compounds of Formulas $IV_b$ and $IV_c$) need not be isolated prior to reaction with the piperazine compound, and/or (ii) the reaction product of the chlorination step (i.e., compound of Formula $V_c$) need not be isolated prior to the bomination step, and/or (iii) the reaction products of the conjugate addition step (i.e., compounds of Formulas $VI_a$ and $VI_b$) need not be isolated from a reaction product mixture comprising them prior to separation (by, e.g., enzymatic resolution).

In one particular embodiment of the present process, all of the above-noted through-process advantages are utilized, in order to reduce the duration of the overall production cycle (as illustrated, for example, in Scheme 3) by about 20%, about 30%, about 40%, about 50%, about 60%, or more, as compared for example to such a process that does not utilize these through-process advantages to prepare an ester substituted analog compound (as illustrated, for example, in Scheme 1). Furthermore, in this particular embodiment, the compound of formula V, is not isolated before bromination, the bromination reaction being carried out using a more reactive brominating agent and more harsh bromination reaction conditions, as further detailed herein. Still further, the bromination reaction is carried out with distillation of the volatile reaction byproducts. Still further, the isomeric mixture comprising the compounds of Formulas $VI_a$ and $VI_b$ is not isolated from the reaction product mixture before being subject to enzymatic resolution. Still further, the bromo-nitrile substituted compounds of Formulas $IV_b$ and $IV_c$ are reacted with the piperazine compound at about room temperature.

The present disclosure is still further directed to one or more of the intermediate reaction products or compounds, or salts thereof, prepared by the process.

A. (Cyclopenta[d]pyrimidin-4-yl)Piperazine Compounds

1. Cyclization Step

In one embodiment, the present disclosure is directed to a process for preparing a compound of Formula I:

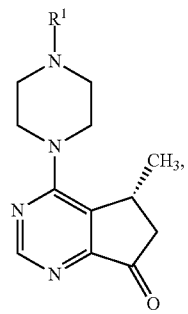

Formula I or a salt thereof, wherein $R^1$ is hydrogen or an amino protecting group. The process comprises contacting a compound of Formula III:

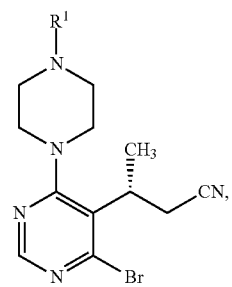

Formula III or a salt thereof, with a metalating agent to form the compound of Formula I, or a salt thereof, wherein R¹ is hydrogen or an amino protecting group. More particularly, the process comprises contacting the compound of Formula III, or a salt thereof, with a metalating agent to form a compound of Formula II:

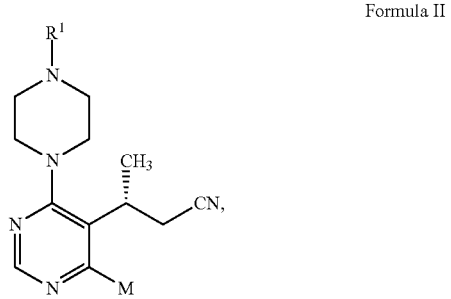

Formula II or a salt thereof, wherein R¹ is as previous defined and M is a metal or transition metal (such as lithium or magnesium) as further detailed below, and then cyclizing the compound of Formula II, or a salt thereof, to form the compound of Formula I, or a salt thereof.

In certain embodiments, R¹ is an amino protecting group, as defined elsewhere herein below. In one or more particular embodiments, R¹ may be selected from phthalimidyl, benzyl, triphenylmethyl, benzylidenyl, p-toluenesufonyl, and p-methoxybenzyl. R¹ may also be selected from —C(O)—R$^d$ or —C(O)OR$^d$, wherein R$^d$ is independently selected from hydrogen, substituted or unsubstituted alkyl, substituted or unsubstituted alkenyl, substituted or unsubstituted alkynyl, substituted or unsubstituted cycloalkyl, substituted or unsubstituted phenyl or substituted or unsubstituted heterocyclyl. Exemplary embodiments include those wherein R¹ is: (i) —C(O)OR$^d$, and further wherein R$^d$ is t-butyl, benzyl or fluorenylmethyl (that is, R¹ is t-butoxycarbonyl (BOC), benzyloxycarbonyl, or fluorenylmethyloxycarbonyl (FMOC)); or, (ii) —C(O)R$^d$, and further wherein R$^d$ is methyl or trifluoromethyl (that is, R¹ is acetyl or trifluoroacetyl). In alternative exemplary embodiments, R¹ is —C(O)OR$^d$ or —C(O)R$^d$, wherein R$^d$ is selected from hydrogen and $C_1$-$C_{10}$ alkyl, and further wherein said alkyl is optionally substituted by an oxo, halo or phenyl moiety. In certain preferred embodiments, R¹ is selected from acetyl, trifluoroacetyl, phthalimidyl, benzyl, triphenylmethyl, benzylidenyl, p-toluenesulfonyl, p-methoxybenzyl, tertbutyloxycarbonyl, 9-fluorenylmethyloxycarbonyl and carbobenzyloxy.

The metalating agent, which is understood to encompass metals and transition metals, may in general be selected from any metalating agent that facilitates cyclization or ring closure to form the cyclopentyl ring. Typically, the metalating agent is an organometal compound, which may for example comprise one or more of lithium and magnesium, and/or a halogen. More particularly, the metalating agent may be an organolithium compound or reagent (e.g., R$^x$Li), an organomagnesium compound or reagent (e.g., R$^x$MgZ), or an organomagnesium-lithium compound or reagent (e.g., (R$^x$)$_3$MgLi), wherein: (i) each R$^x$ present is independently selected from optionally substituted $C_{1-10}$ alkyl, optionally substituted $C_{3-7}$ cycloalkyl, optionally substituted aryl, optionally substituted heteroaryl, or optionally substituted heterocyclyl, or two R$^x$ groups are taken together with the atom to which they are attached to form a 5-7 membered, optionally substituted ring; and, (ii) Z is a halogen, and more particularly is Cl, Br or I. In some embodiments, each R$^x$ is independently selected from optionally substituted $C_{1-10}$ alkyl and optionally substituted $C_{3-7}$ cycloalkyl, but more particularly is selected from isopropyl (iPr) or butyl (n-butyl, sec-butyl or t-butyl). Optionally, an additive that acts to modulate the reactivity and/or the stability of the metalating agent may also be used (e.g., an amine, and more specifically a diamine, additive or modifier).

Exemplary organomagnesium compounds or reagents include Grignard reagents like $C_1$-$C_6$ alkylmagnesium halides, and more particularly include iPrMgCl or sec-butylMgCl, which may be used alone or as part of a lithium chloride complex (e.g., iPrMgCl.LiCl). (See, e.g., *Organomet. Chem.*, 2011, 37, 1-26, pp. 7-13; and, A. Krasovskiy and P. Knochel, *Angew. Chem., Int. Ed.*, 2004, 43, 333.) Exemplary organolithium compounds or reagents include $C_1$-$C_6$ alkyllithium, and more particularly include n-butyllithium, sec-butyllithium and t-butyllithium. Exemplary organomagnesium-lithium compounds or reagents (i.e., (R$^x$)$_3$MgLi), include those wherein R$^x$ is $C_1$-$C_6$ alkyl, and more particularly is for example isopropyl or butyl (e.g., n-butyl, sec-butyl or t-butyl), such compounds including lithium tri-n-butylmagnesiate, lithium triisopropylmagnesiate, and lithium (isopropyl)(di-n-butyl)magnesiate.

Although the particular process conditions, including one or more of reaction time, temperature, solvent, reagent, amount of reagent(s), order of reagent addition, pH, etc. may be selected in order to optimize reaction product purity and/or yield, in particular the compound of Formula III may be contacted with from about 1 to about 1.5 molar equivalents of the metalating agent, and more particularly from about 1 to about 1.4, or from about 1.05 to about 1.2, molar equivalents of the metalating agent. Additionally, in one particular embodiment, the action of combining or contacting the compound of Formula III with the metalating agent may occur over a period of time or in stages during this reaction step, the amount and/or timing of each addition being determined in order to optimize yield and/or purity, and/or to ensure the final addition occurs near the end of the reaction time. For example, the metalating agent may be added in about equal portions to the reaction mixture containing the compound of Formula III over a period of time (e.g., about 4 hours), the final portion thereof being added near the end of the desire reaction time.

In various embodiments, the process for preparing the compound of Formula I, or a salt thereof, may be carried out in an ethereal or hydrocarbon solvent, or a mixture of these solvents (e.g., tetrahydrofuran (THF), 2-methyltetrahydrofuran (MeTHF), methyl tert-butyl ether (MTBE), cyclopentyl methyl ether (CPME), diethyl ether, diisopropyl ether, diphenyl ether, toluene, ethylbenzene, xylene, cumene, pentane or heptane). Exemplary reaction conditions include: (i) a reaction temperature of about 20° C., about 15° C., about 10° C., about 5° C., about 0° C., or less (e.g., about –10° C., about –25° C., about –50° C., or about –75° C.); and/or (ii) carrying out the reaction under substantially anhydrous conditions (e.g., about 100 ppm, about 50 ppm, about 25 ppm, or about 10 ppm water, or less); and/or (iii) carrying out the reaction under an inert atmosphere (e.g., under a helium, neon, argon or nitrogen atmosphere). In a particular embodiment, a process for preparing a compound of Formula I, or a salt thereof, from a compound of Formula III, or salt thereof, is carried out in MeTHF, alone or in combination with toluene, at a temperature of from about –15° C. to about 15° C., from about –10° C. to about 10° C., or from about 0° C. to about 5° C., optionally under anhydrous conditions and/or optionally under an inert (e.g., nitrogen) atmosphere.

Additionally, it is to be understood that further processing or work up of one or more of the resulting products from the above-note cyclization or ring closure reaction may be performed, in order to obtain the desired final product (i.e., the compound of Formula I) using means known in the art, such as for example hydrolysis of an enamine reaction intermediate to obtain the final ketone product. See, e.g., WO 2013/173784, the contents of which are incorporated by reference for all relevant and consistent purposes.

In various embodiments, conversion or cyclization of the compound of Formula III to the compound of Formula I is about 90%, about 95%, about 99% or more, and/or the yield of the compound of Formula I is about 75%, about 80%, about 85%, about 90% or more.

2. Piperazine Addition Step

In one embodiment, the compound of Formula III, or a salt thereof, is prepared by contacting a compound of Formula IV:

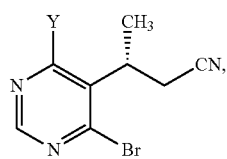

Formula IV or salt thereof, wherein Y is selected from chloro and bromo, with a piperazine compound having the structure:

or salt thereof, wherein Lv is a leaving group and $R^1$ is an amino protecting group, both as defined elsewhere herein below. In an exemplary embodiment, Y is bromo. In this or another exemplary embodiment, $R^1$ may be, for example, alkoxycarbonyl (such as t-butoxycarbonyl) or aryloxycarbonyl (such as benzyloxycarbonyl). In these or other exemplary embodiments, Lv may be, for example, hydrogen or halogen. Alternatively, however, one or both of $R^1$ and Lv may be selected from among the other options recited in the definitions provided elsewhere herein below, or alternatively from amino protecting groups and leaving groups known to those of skill in the art, without departing from the intended scope of the present disclosure.

Although the particular process conditions, including reaction time, temperature, solvent, reagent, amount of reagent(s), order of reagent addition, pH, etc. may be selected in order to optimize reaction product purity and/or yield, in particular the compound of Formula IV may be contacted with from about 1 to 1.5 molar equivalents of the piperazine compound, and more typically will be contacted with from about 1.05 to about 1.4, or from about 1.1 to about 1.2, molar equivalents of the piperazine compound, with about 1.15 equivalents of the piperazine compound being used in one particular embodiment.

In this regard it is to be noted that reaction temperature and/or the amount of the piperazine compound added, among other considerations (e.g., type and/or amount of base added or solvent used), will typically be controlled or optimized in order to limit the amount of a di-piperazine substituted reaction byproduct being formed (i.e., the formation of a compound wherein both bromine atoms are displaced by or exchanged with the piperazine compound). For example, in one or more embodiments the reaction is carried out at a temperature of less than about 60° C., 50° C., 40° C., or even 30° C., with the reaction in one particular embodiment being carried out at about room temperature (e.g., about 20° C. or about 25° C.), using for example N,N-diisopropylethylamine (DIEA) as a base (e.g., about 1.5, about 1.75, about 2, or more molar equivalents thereof), and acetonitrile ($CH_3CN$) as a solvent (alone or in combination with water).

In various embodiments, the yield of compound of Formula III is about 85%, about 90%, about 95% or more, and/or the purity thereof is about 90%, about 95%, about 98% or more.

3. Bromination Step

In one embodiment, the compound of Formula IV, or a salt thereof, is prepared by brominating a compound of Formula V:

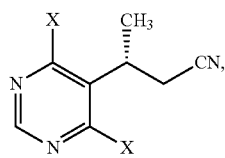

Formula V or salt thereof; wherein each X is independently selected from chloro and hydroxyl. In a particular embodiment, both of the X substituents are hydroxyl, while in another embodiment both of the X substituents are chloro.

In this regard it is to be noted that, in some instances, the resulting reaction mixture may contain both the di-bromo substituted compound of Formula IV, as well as a bromo-chloro substituted analogue compound, which if present will be the minor reaction product. Generally, the molar ratio of the di-bromo compound to the bromo-chloro compound will be, for example, about 95:1, about 96:1, about 97:1, about 98:1, or more. More particularly, when a di-chloro compound of Formula V is subjected to bromination, the resulting reaction mixture may contain both the compound of Formula IV$_b$ (wherein Y in Formula IV is bromo), as well as the compound of Formula IV$_c$ (wherein Y in Formula IV is chloro):

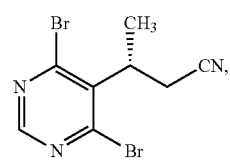

Formula IV$_b$

-continued

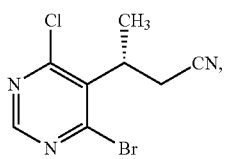

Formula IV$_c$ the molar ratio of the two compounds being as noted above.

The brominating agent for the reaction is selected from among known bromination agents that, when contacted with the compound of Formula V under appropriate reaction conditions, results in the formation of a volatile byproduct, and more specifically a byproduct that can be removed from the reaction mixture by distillation. In this regard, it is generally believed that removal of these byproducts from the mixture, as the reaction is carried out, enables the equilibrium of the reaction to be better controlled, such that the reaction favors halogen (i.e., bromine) exchange at both locations, and more particularly that both X moieties in the compound of Formula V (i.e., both chlorine atoms in the compound of Formula V$_c$, or both hydroxyl moieties in the compound of Formula V$_b$) are replaced with bromine atoms. Such an approach enables greater conversion to the desired reaction product, and reduces the amount of impurities that are otherwise formed.

Exemplary brominating agents include, but are not limited to, bromine, bromotrimethylsilane (or trimethylsilyl bromide (TMSBr)), phosphorus oxybromide (POBr$_3$), N-bromosuccinimide (NBS), and phosphorus tribromide (PBr$_3$).

In this regard it is to be noted that the brominating agent may be added to the reaction mixture, or alternatively may be formed in situ, using methods generally known in the art. For example, TMSBr could be made in situ by the addition of trimethylsilyl chloride (TMSCl) and sodium bromide (NaBr), or another alkali metal bromide (e.g., KBr, LiBr, MgBr$_2$, ZnBr$_2$, or tetraalkylammonium bromide), to the reaction mixture.

Although the particular process conditions, including reaction time, temperature, solvent, reagent, amount of reagent(s), order of reagent addition, pH, etc. may be selected in order to optimize reaction product purity and/or yield, in particular the compound of Formula V will be contacted with from about 2 to about 7 molar equivalents of the brominating agent, and more typically will be contacted with from about 2.5 to about 6, or from about 3 to about 5, molar equivalents of the brominating agent, with about 3.5 equivalents of brominating agent being used in one particular embodiment, the brominating agent being added in a single aliquot or in multiple aliquots over a period of time. Additionally, or alternatively, reaction may be carried out at a temperature of from about 65° C. to about 80° C., or from about 70° C. to about 75° C., using for example acetonitrile (CH$_3$CN) as a solvent, for about 15 hours to about 20 hour, or about 16 hours to about 18 hours.

In various embodiments, conversion of the compound of Formula V to the compound of Formula IV is about 85%, about 90%, about 95% or more.

4. Chlorination Step

The compound of Formula IV, or salt thereof, may be prepared by directly brominating the compound or salt of Formula V, using for example phosphorus oxybromide or phosphorus tribromide, or alternatively a compound of Formula V$_b$ or a salt thereof, below. In one particular embodiment, however, the compound of Formula IV, or salt thereof, is prepared by first chlorinating the compound of Formula V$_b$:

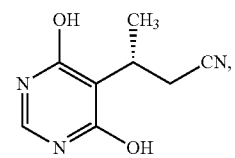

Formula V$_b$ or a salt thereof, to form a compound of Formula V$_c$:

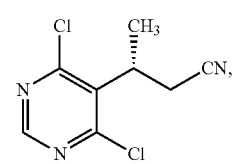

Formula V$_c$ or a salt thereof, and then brominating the compound or salt of Formula V$_c$ to form the compound or salt of Formula IV as detailed above.

The particular process conditions, including reaction time, temperature, solvent selection, reagent, amount of reagent(s), order of reagent addition, pH, etc. may be selected in order to optimize reaction product purity and/or yield. For example, in various embodiments the compound of Formula V$_b$ will be contacted with from about 1.5 to about 5 molar equivalents of the chlorinating agent, and more typically will be contacted with from about 2 to about 4, or from about 2.5 to 3.5, molar equivalents of the chlorinating agent, with about 3 equivalents of chlorinating agent being used in one particular embodiment. In these or other embodiments, suitable chlorinating agents include, for example, phosphorus oxychloride (POCl$_3$) and phosphorus trichloride (PCl$_3$), among others. In these or still other embodiments, the reaction may be carried out neat, the chlorinating agent (e.g., POCl$_3$) being added with an appropriate amount of base, such as about 1, about 1.1, about 1.2, or more molar equivalents of for example 2,6-lutidine or N,N-dimethyl aniline, in the absence of a solvent. Alternatively, selection of a base and/or solvent (e.g., 2,6-lutidine with toluene as a solvent) may enable through-processing to be achieved, as further discussed elsewhere herein.

5. Pyrimidine Synthesis Step

In accordance with the present disclosure, the pyrimidine compound of Formula V$_b$, or salt thereof, is prepared by cyclizing a compound of Formula VI$_b$:

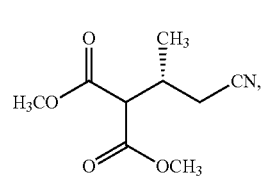

Formula VI$_b$ or a salt thereof. The process comprises contacting the compound of Formula VI$_b$, or salt thereof, with formamidine, and more particularly a salt thereof, including for example an acetate salt (i.e., formamidine acetate).

The particular process conditions, including reaction time, temperature, solvent selection, reagent, amount of reagent(s), order of reagent addition, pH, etc. may be selected in order to optimize reaction product purity and/or yield. For example, in various embodiments, the reaction may be carried out in an alcohol solvent (e.g., methanol). In these or other embodiments, the compound of Formula VI$_b$, or salt thereof, is contacted with from about 1 to about 1.25 molar equivalents of the formamidine, and more typically will be contacted with from about 1 to about 1.15, or from about 1 to about 1.05, molar equivalents of the formamidine, with about 1.05 equivalents of formamidine being used in one particular embodiment. Additionally, about 2, about 2.5, about 3, or more molar equivalents of a base, such as NaOMe, may also be used in the reaction.

In various embodiments, the yield of the compound of Formula V$_b$, or salt thereof, is about 75%, about 80%, about 85% or more.

6. Conjugate Addition and Enzymatic Resolution Steps

Additionally, the compound of Formula VI$_b$, or a salt thereof, is prepared by contacting crotononitrile with malonate to form an isomeric mixture of a compound of Formula VI$_a$ and a compound of Formula VI$_b$:

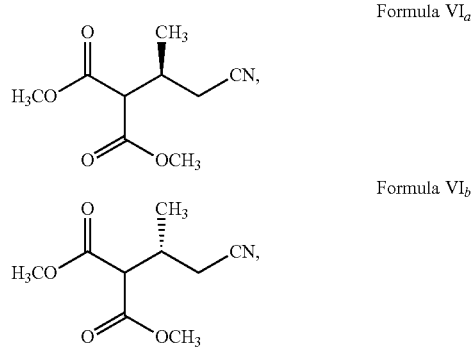

or salts thereof; and separating the compound or salt of Formula VI$_b$ from the compound or salt of Formula VI$_a$.

The particular process conditions, including reaction time, temperature, solvent selection, reagent, amount of reagent(s), order of reagent addition, pH, etc. may be selected in order to optimize reaction product purity and/or yield. For example, in various embodiments, the reaction of crotononitrile with malonate may be carried out in an alcohol solvent (e.g., methanol), or in a solvent such as tetrahydrofuran (THF). In these or other embodiments, the crotononitrile is contacted with from about 1 to about 1.5 molar equivalents of the malonate, and more typically will be contacted with from about 1.05 to about 1.4, or from about 1.1 to about 1.3, molar equivalents of the malonate, with about 1.1 equivalents of malonate being used in one particular embodiment. Additionally, from about 0.2 to about 0.8, or from about 0.4 to about 0.6, molar equivalents of a base, such as sodium methoxide (NaOMe), sodium tert-pentoxide (or sodium tert-amylate, t-AmONa), and potassium tert-pentoxide, may be added, with about 0.5 molar equivalents of base being used in one particular embodiment.

In various embodiments, the yield of the compound of Formula VI$_a$, or salt thereof, is about 70%, about 75%, about 80% or more.

The compound of Formula VI$_b$, or salt thereof, may be separated from the compound of Formula VI$_a$, or salt thereof, using techniques generally known in the art for the separation of isomers. In one particular embodiment, however, the compound of Formula VI$_b$, or salt thereof, is separated from the isomeric mixture containing it and the compound of Formula VI$_a$, or salt thereof, by enzymatic resolution. Enzymatic resolution of the isomeric mixture may be achieved using techniques generally known in the art, including for example contacting the isomeric mixture with a suitable lipase enzyme, in order to selectively hydrolyze an ester moiety of the compound of Formula VI$_a$, or salt thereof, such that the compound of Formula VI$_b$, or salt thereof, may be separated from the hydrolyzed compound. Suitable lipase enzymes include, for example, those enzymes originated from a microorganism of Candida, such as Candida cylindracea and Candida rugosa, a microorganism of Chromobacterium chocolatum, pig liver and a thermophilic microorganism. Other suitable lipase enzymes are referenced in, for example, WO 2013/173736 (the entire contents of which are incorporated herein by reference for all relevant and consistent purposes), as well as in Examples 2b and 2c herein. Alternatively, and more particularly, enzymatic resolution of the isomeric mixture may be achieved by contacting the isomeric mixture with a suitable nitrilase enzyme, in order to selectively hydrolyze the nitrile moiety of the compound of Formula VI$_a$, or salt thereof, such that the compound of Formula VI$_b$, or salt thereof, may be separated from the hydrolyzed compound. Suitable nitrilase enzymes include, for example, the enzyme referenced in Example 2a, 2d and 2e herein.

The particular process techniques and conditions for the separation, and more particularly the enzymatic resolution, of the compound or salt of Formula VI$_b$ from the compound or salt of Formula VI$_a$, including enzyme type, reaction time, temperature, solvent selection, reagent, amount of reagent(s), order of reagent addition, pH, etc. may be selected in order to optimize desired product purity and/or yield and/or reaction time. For example, in various embodiments, a mixture comprising the compounds of Formulas IV$_a$ and IV$_b$, or salts thereof, a nitrilase enzyme, a solvent (such as water), a base (such as NaOH), and/or a buffer (such as KH$_2$SO$_4$ or K$_2$SO$_4$ or Na$_2$B$_4$O$_7$.10H$_2$O), may be used to carry out the enzymatic resolution at about room temperature (e.g., about 20-25° C.), over a period of about 24 hour, about 36 hours, about 48 hours or more, with a period of from about 24 to about 48 hour being typically used in one or more embodiments.

In various embodiments, the yield of the compound of Formula VI$_b$, or salt thereof, is about 30%, about 35%, about 40%, about 45% or more.

7. Through-Process Improvements and Overall Process Efficiency

For purposes of illustration, Scheme 4 below generally illustrates a representative embodiment of the process of the present disclosure, as well as various compounds and intermediates encompassed by the present disclosure. More detailed embodiments, including specific process conditions and regents, are further provided in the Examples that follow. Those skilled in the art will appreciate that other reaction conditions, including reagents, reagent concentrations or molar equivalents, solvents, reaction temperature, reaction duration, etc., as well as needed work-up (e.g., acid or base treatment), may be used consistent with the present process, in order to obtained the desired compounds and intermediates, without departing from the intended scope of the present disclosure. Accordingly, the details presented here should not be viewed in a limiting sense.

IV (i.e., IV$_b$ and IV$_c$), or salts thereof, are not isolated after the bromination of the compound of Formula V$_c$, or salt thereof, before reaction with the piperazine compound, as detailed above. In those embodiments wherein this three-step reaction sequence is carried out without isolation of the noted intermediates (i.e., chlorination, bromination and pip-

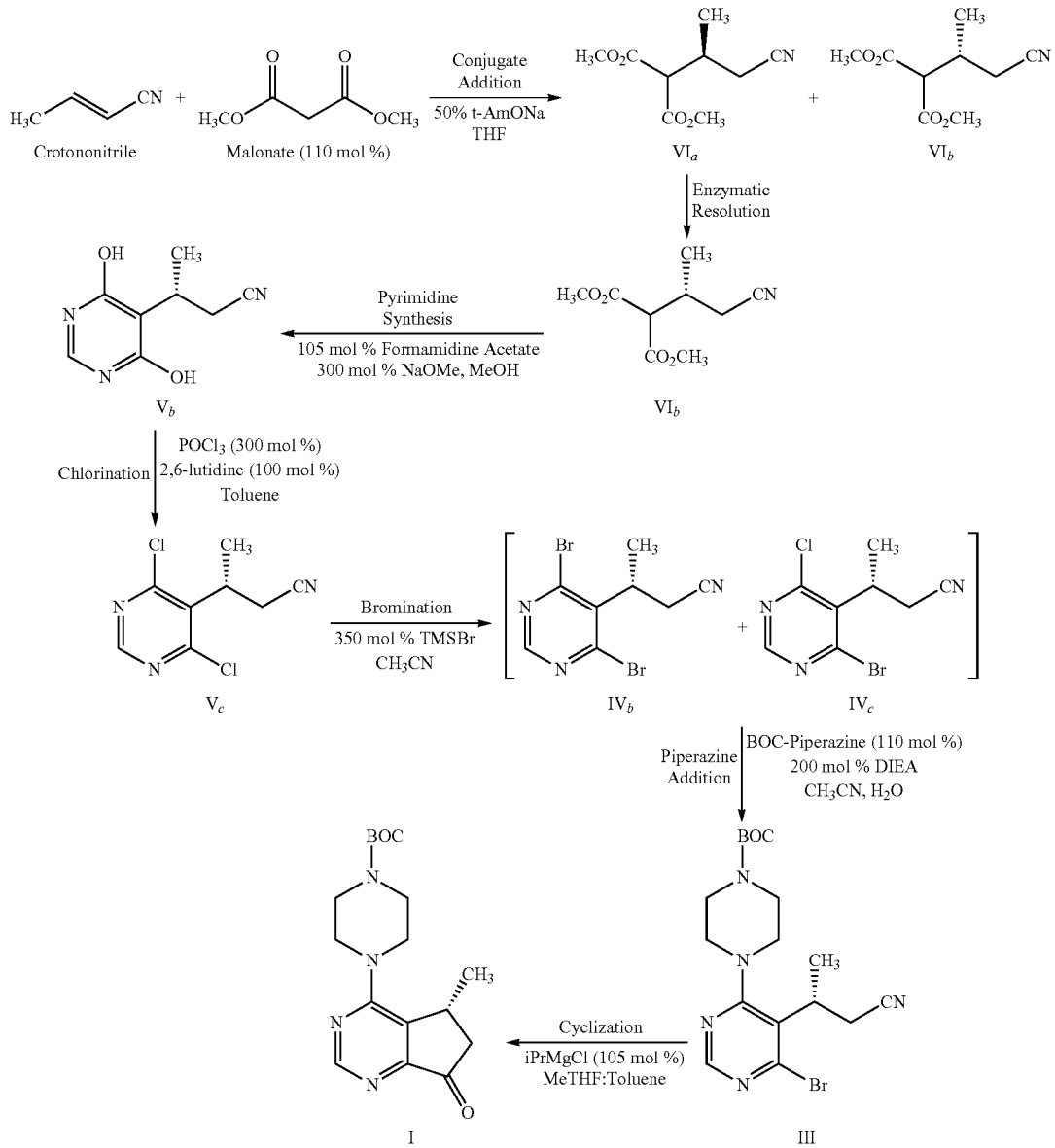

Scheme 4

It is to be noted that the process of the present disclosure is particularly advantageous because two or more of the process steps, as illustrated for example in Scheme 4 above, may be carried out in series or sequence, without isolation of the intermediate reaction product.

In one particular embodiment, after the chlorination of the compound of Formula V$_b$, or salt thereof, the resulting compound of Formula V$_c$, or salt thereof, is not isolated before it is subjected to bromination to form the compounds of Formula IV (i.e., IV$_b$ and IV$_c$), or salts thereof. In this or another particular embodiment, the compounds of Formula erazine addition reactions are carried out without isolation of the compounds of Formula V$_c$, IV$_b$/IV$_c$ and III, or salts thereof, respectively), the average yield is typically about 80%, about 85%, about 90%, about 95% or more. In this or yet another particular embodiment, the isomeric mixture comprising the compounds of Formula VI$_a$ and Formula VI$_b$, or salts thereof, is not isolated from the reaction product mixture prior to further separation of the compound of Formula VI$_b$ or salt thereof, from the compound of Formula VI$_a$ or salt thereof; that is, the compounds of Formula VI$_a$ and Formula VI$_b$, or salts thereof, are not isolated prior to reaction of the compound of Formula VI$_a$ or salt thereof with a suitable enzyme (e.g., a nitrilase enzyme), in order to separate the compound of Formula VI$_b$ or salt thereof from it.

Accordingly, the present disclosure advantageously provides or enables the above-noted through-process reaction steps to be carried out, thus eliminating the need to isolate multiple reaction intermediates (e.g., chlorination/bromination being performed through-process, bromination/piperazine addition being performed through-process, chlorination/bromination/piperazine addition being performed through-process, the enzymatic resolution being performed through-process, or all of these noted reactions steps being performed through-process).

In one exemplary embodiment of the present process, all of the above-noted through process steps are utilized; that is, the enzymatic resolution step, as well as the chlorination/bromination/piperazine addition steps, are performed through-process, wherein the various reaction products being formed by each step are not be isolated before the next reaction step is carried out. The present process therefore advantageously enables significant improvements in process efficiency. For example, the average duration of the overall production cycle of the present process (as illustrated, for example, by Scheme 4) is reduced, as compared for example to the average duration of the overall production cycle for such a process that does not utilize these through-process advantages to prepare an ester substituted analog compound (as illustrated, for example, by Scheme 1), by about 30%, about 40%, about 50%, about 60%, about 70%, or more, due to fewer process steps being utilized (e.g., fewer isolation steps), and/or shorter reaction times (e.g., less time needed for enzymatic resolution using a nitrilase enzyme, as compared for example to enzymatic resolution using a lipase enzyme). In another embodiment, enzymatic resolution using a nitrilase enzyme at elevated pH (for example pH about 9.2) exhibits about double reaction rate and higher selectivity (E) as compared to nitrilase resolution having starting pH about 7.2 or resolution using a lipase enzyme.

8. Exemplary Embodiments

In a first exemplary embodiment of the present disclosure, the compound of Formula I:

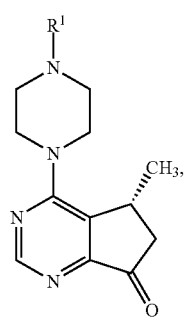

Formula I or a salt thereof, wherein R$^1$ is hydrogen or an amino protecting group, is prepared by a process comprising: (a) contacting a compound of compound of Formula IV:

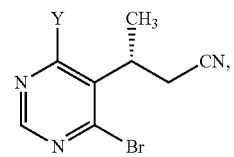

Formula IV or salt thereof, wherein Y is selected from chloro and bromo, with a piperazine compound having the structure:

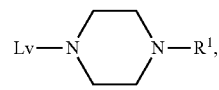

or salt thereof, wherein Lv is a leaving group and R$^1$ is an amino protecting group, to form a compound of Formula III:

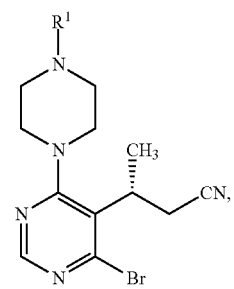

Formula III or a salt thereof; and, (b) contacting the compound of Formula III, or a salt thereof, with a metalating agent to form the compound of Formula I, or a salt thereof.

In one aspect of the first exemplary embodiment, R$^1$ is H, or is an amino protecting group selected from t-butoxycarbonyl, benzyloxycarbonyl, and fluorenylmethyloxycarbonyl. In another aspect, Y is bromo. In another aspect, Lv is hydrogen or halogen. In another aspect, the compound of Formula IV, or a salt thereof, is contacted with about 1 to about 1.5, or about 1.1 to about 1.2, molar equivalents of the piperazine compound, and in another aspect this reaction is carried out at about room temperature. In another aspect, the compound of Formula III, or a salt thereof, is contacted with about 1 to about 1.5, or about 1.05 to about 1.2, molar equivalents of the metalating agent, and in another aspect the metalating agent is a Grignard reagent selected from an organomagnesium halide and an organolithium reagent.

In a second exemplary embodiment of the present disclosure, the compound of Formula I:

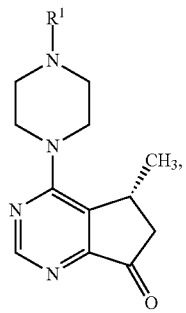

Formula I or a salt thereof, wherein $R^1$ is hydrogen or an amino protecting group, is prepared by a process comprising: (a) brominating a compound of Formula V:

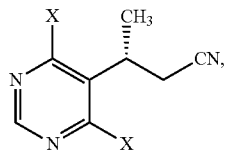
Formula V or salt thereof, wherein each X is independently selected from chloro and hydroxyl, to form a compound of Formula IV:

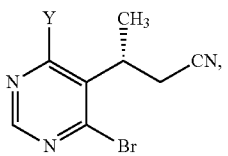
Formula IV or salt thereof, wherein Y is selected from chloro and bromo; (b) contacting the compound of Formula IV, or a salt thereof, with a piperazine compound having the structure:

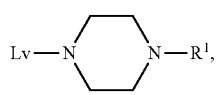

or salt thereof, wherein Lv is a leaving group and $R^1$ is an amino protecting group, to form a compound of Formula III:

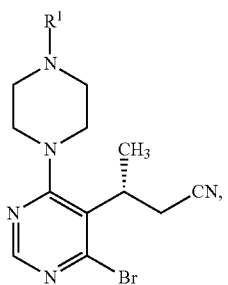
Formula III or a salt thereof; and, (c) contacting the compound of Formula III, or a salt thereof, with a metalating agent to form the compound of Formula I, or a salt thereof.

In one aspect of the second exemplary embodiment, $R^1$ is H, or is an amino protecting group selected from t-butoxycarbonyl, benzyloxycarbonyl, and fluorenylmethyloxycarbonyl. In another aspect, X is chloro. In another aspect, Y is bromo. In another aspect, Lv is hydrogen or halogen. In another aspect, the compound of Formula V, or a salt thereof, is contacted with about 2 to about 7, or about 3 to about 5, molar equivalents of a brominating agent, and in another aspect the brominating agent is trimethylsilyl bromide. In another aspect, the bromination reaction is carried out at about 70° C. to about 75° C., and in another aspect distillation is used to remove volatile byproducts. In another aspect, the compound of Formula IV, or a salt thereof, is contacted with about 1 to about 1.5, or about 1.1 to about 1.2, molar equivalents of the piperazine compound, and in another aspect this reaction is carried out at about room temperature. In another aspect, the compound of Formula III, or a salt thereof, is contacted with about 1 to about 1.5, or about 1.05 to about 1.2, molar equivalents of the metalating agent, and in another aspect the metalating agent is a Grignard reagent selected from an organomagnesium halide and an organolithium reagent. In another aspect, the compound of Formula IV, or salt thereof, is not isolated after the bromination reaction and before reaction with the piperazine compound.

In a third exemplary embodiment of the present disclosure, the compound of Formula I:

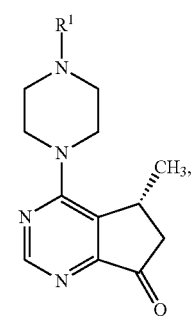
Formula I or a salt thereof, wherein $R^1$ is hydrogen or an amino protecting group, is prepared by a process comprising: (a) chlorinating a compound of Formula $V_b$:

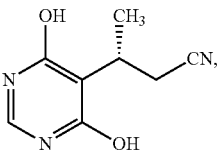
Formula $V_b$ or a salt thereof, to form a compound of Formula $V_c$:

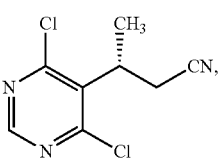
Formula $V_c$ or a salt thereof; (b) brominating the compound of Formula $V_c$, or salt thereof, to form the compound of Formula IV:

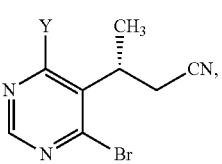
Formula IV or salt thereof, wherein Y is selected from chloro and bromo; (c) contacting the compound of Formula IV, or a salt thereof, with a piperazine compound having the structure:

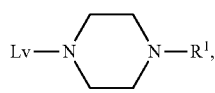

or salt thereof, wherein Lv is a leaving group and $R^1$ is an amino protecting group, to form a compound of Formula III:

Formula III

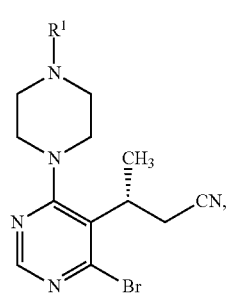

or a salt thereof; and, (d) contacting the compound of Formula III, or a salt thereof, with a metalating agent to form the compound of Formula I, or a salt thereof.

In one aspect of the third exemplary embodiment, $R^1$ is H, or is an amino protecting group selected from t-butoxycarbonyl, benzyloxycarbonyl, and fluorenylmethyloxycarbonyl. In another aspect, Y is bromo. In another aspect, Lv is hydrogen or halogen. In another aspect, the compound of Formula $V_b$, or a salt thereof, is contacted with about 1.5 to about 5, or about 2 to about 4, molar equivalents of a chlorinating agent, and in another aspect the chlorinating agent is phosphorus oxychloride. In another aspect, the compound of Formula V, or a salt thereof, is contacted with about 2 to about 7, or about 3 to about 5, molar equivalents of a brominating agent, and in another aspect the brominating agent is trimethylsilyl bromide. In another aspect, the bromination reaction is carried out at about 70° C. to about 75° C., and in another aspect distillation is used to remove volatile byproducts. In another aspect, the compound of Formula IV, or a salt thereof, is contacted with about 1 to about 1.5, or about 1.1 to about 1.2, molar equivalents of the piperazine compound, and in another aspect this reaction is carried out at about room temperature. In another aspect, the compound of Formula III, or a salt thereof, is contacted with about 1 to about 1.5, or about 1.05 to about 1.2, molar equivalents of the metalating agent, and in another aspect the metalating agent is a Grignard reagent selected from an organomagnesium halide and an organolithium reagent. In another aspect, the compound of Formula IV, or salt thereof, is not isolated after the bromination reaction and before reaction with the piperazine compound. In another aspect, the compound of Formula $V_c$, or salt thereof, is not isolated after the chlorination reaction and before the bromination reaction.

In a fourth exemplary embodiment of the present disclosure, the compound of Formula I:

Formula I

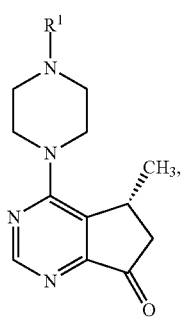

or a salt thereof, wherein $R^1$ is hydrogen or an amino protecting group, is prepared by a process comprising: (a) contacting crotononitrile with malonate to form an isomeric mixture comprising a compound of Formula $VI_a$ and the compound of Formula $VI_b$:

Formula $VI_a$

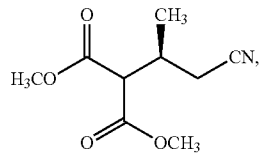

Formula $VI_b$

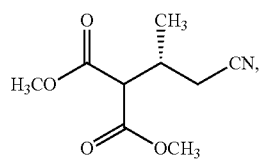

or salts thereof; (b) separating the compound of Formula $VI_b$, or salt thereof, from the compound Formula $VI_a$, or salt thereof, in the isomeric mixture; (c) contacting the separated compound of Formula $VI_b$, or salt thereof, with a formamidine salt to form the compound of Formula $V_b$:

Formula $V_b$

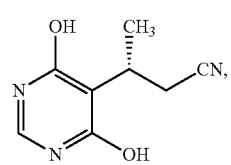

or a salt thereof; (d) chlorinating the compound of Formula $V_b$ or a salt thereof, to form a compound of Formula $V_c$:

Formula $V_c$

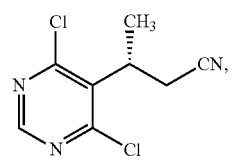

or a salt thereof; (e) brominating the compound of Formula $V_c$, or salt thereof, to form the compound of Formula IV:

Formula IV

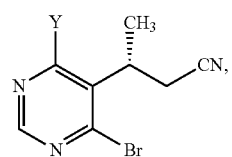

or salt thereof, wherein Y is selected from chloro and bromo; (f) contacting the compound of Formula IV, or a salt thereof, with a piperazine compound having the structure:

or salt thereof, wherein Lv is a leaving group and $R^1$ is an amino protecting group, to form a compound of Formula III:

Formula III

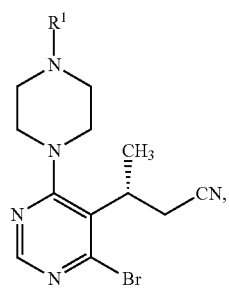

or a salt thereof; and, (g) contacting the compound of Formula III, or a salt thereof, with a metalating agent to form the compound of Formula I, or a salt thereof.

In one aspect of the fourth exemplary embodiment, $R^1$ is H, or is an amino protecting group selected from t-butoxycarbonyl, benzyloxycarbonyl, and fluorenylmethyloxycarbonyl. In another aspect, Y is bromo. In another aspect, Lv is hydrogen or halogen. In another aspect, the crotononitrile is contacted with about 1 to about 1.5, or about 1.1 to about 1.3, molar equivalents of malonate. In another aspect, the compound of Formula $VI_b$, or salt thereof, is separated from the compound Formula $VI_a$, or salt thereof, in the isomeric mixture by enzymatic resolution, and in another aspect the compound of Formula $VI_b$, or salt thereof, is separated by contacting the isomeric mixture with a nitrilase enzyme. In another aspect, the separated compound of Formula $VI_b$, or salt thereof, is contacted with about 1 to about 1.25, or about 1 to about 1.15, molar equivalents of a formamidine salt to form the compound of Formula $V_b$, and in another aspect the formamidine salt is formamidine acetate. In another aspect, the compound of Formula $V_b$, or a salt thereof, is contacted with about 1.5 to about 5, or about 2 to about 4, molar equivalents of a chlorinating agent, and in another aspect the chlorinating agent is phosphorus oxychloride. In another aspect, the compound of Formula V, or a salt thereof, is contacted with about 2 to about 7, or about 3 to about 5, molar equivalents of a brominating agent, and in another aspect the brominating agent is trimethylsilyl bromide. In another aspect, the bromination reaction is carried out at about 70° C. to about 75° C., and in another aspect distillation is used to remove volatile byproducts. In another aspect, the compound of Formula IV, or a salt thereof, is contacted with about 1 to about 1.5, or about 1.1 to about 1.2, molar equivalents of the piperazine compound, and in another aspect this reaction is carried out at about room temperature. In another aspect, the compound of Formula III, or a salt thereof, is contacted with about 1 to about 1.5, or about 1.05 to about 1.2, molar equivalents of the metalating agent, and in another aspect the metalating agent is a Grignard reagent selected from an organomagnesium halide and an organolithium reagent. In another aspect, the compound of Formula IV, or salt thereof, is not isolated after the bromination reaction and before reaction with the piperazine compound. In another aspect, the compound of Formula $V_c$, or salt thereof, is not isolated after the chlorination reaction and before the bromination reaction. In another aspect, the compounds of Formulas $VI_b$ and $VI_a$, or salts thereof, in the isomeric mixture are not isolated before enzymatic resolution.

B. AKT Inhibitor Synthesis

The present disclosure is still further directed to the use of the compounds of Formula I, or a salt thereof, as an intermediate in the synthesis of Ipatasertib (i.e., (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)-propan-1-one), as disclosed for example in U.S. Pat. No. 8,063,050 (see, e.g., Example 14 therein). Scheme 5 below generally illustrates an embodiment of the process of the present disclosure, as well as various compounds and intermediates encompassed by the present disclosure, wherein the compound of Formula I, or a salt thereof, is used to prepare Ipatasertib, in protected or unprotected form, or a salt thereof.

Scheme 5

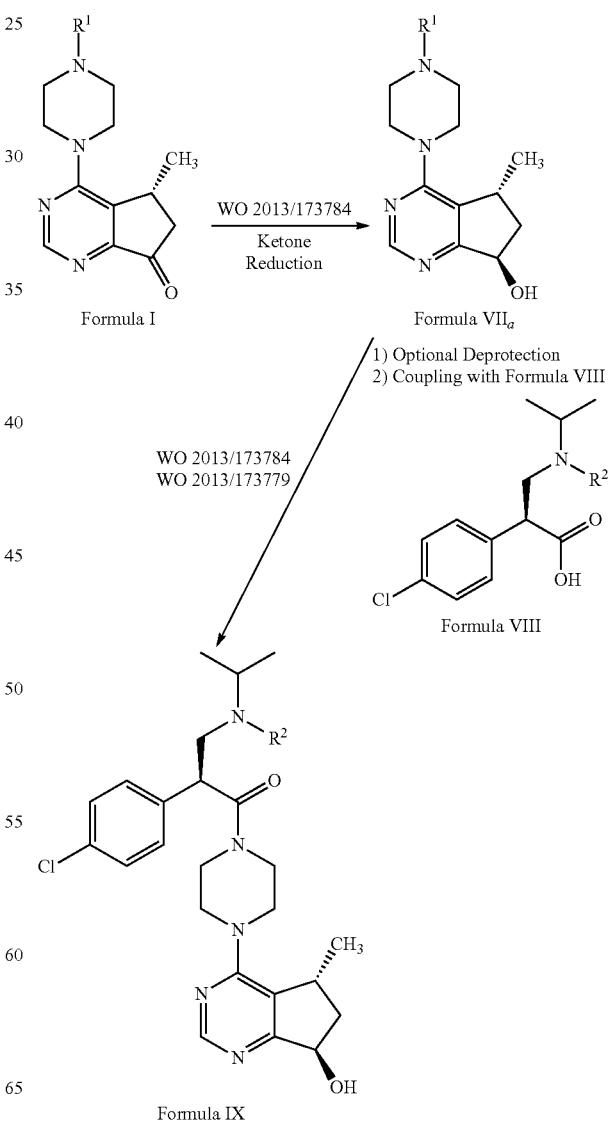

In particular, the compounds of Formula I, or a salt thereof, may be used to prepare a compound of Formula IX, or a salt thereof (i.e., Ipatasertib, in protected or unprotected form, or a salt thereof):

Formula IX

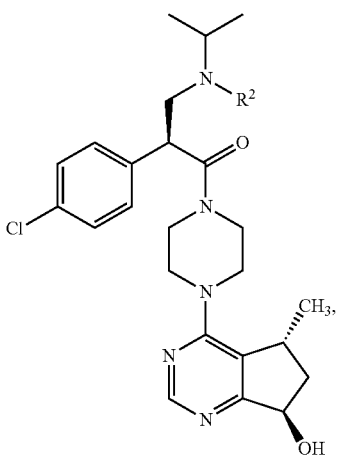

wherein $R^2$ is hydrogen or an amino protecting group, as defined elsewhere herein below, and more particularly as defined in the context of $R^1$ above.

In this regard it is to be noted that various suitable reaction schemes and processes may be used in accordance with the present disclosure, in order to convert the compound of Formula I, or a salt thereof, to a compound of Formula IX, or a salt thereof. In one particular embodiment, however, the process comprises first preparing the compound of Formula I, or a salt thereof, as set forth above. The compound of Formula I, or salt thereof, is then reduced to form a compound of Formula VII$_a$:

Formula VII$_a$

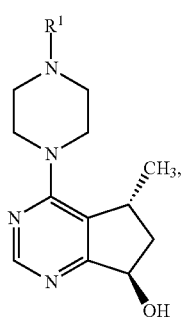

or salt thereof. More particularly, the compound of Formula I, or salt thereof, is subjected to stereoselective reduction by contacting it with a reducing agent comprising a suitable enzyme, such as a ketoreductase enzyme, and optionally a hydride source, as disclosed in for example WO 2013/173784 (the contents of which are incorporated herein by reference for all relevant and consistent purposes), in order to obtain the isomer of Formula VII$_a$.

If $R^1$ is a protecting group, the compound of Formula VII$_a$, or salt thereof, may be deprotected using means generally known in the art (e.g., reacting with a suitable acid, such as hydrochloric acid) to form a compound of Formula VII$_b$, Formula VII$_b$

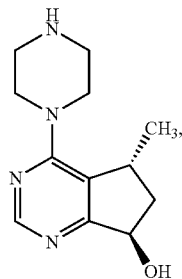

or salt thereof. The compound of Formula VII$_b$, or salt thereof, is then contacted with a compound of Formula VIII:

Formula VIII

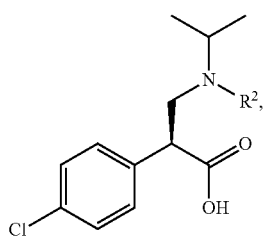

or salt thereof, to obtain the compound of Formula IX. The coupling of the compound of Formula VII$_b$, or salt thereof, with the compound or salt of Formula VIII, may be achieved using means known in the art, and/or as disclosed in for example WO 2013/173784 or WO 2013/173779, and in one embodiment may include the use of a suitable coupling agent as disclosed therein. Additionally, the method of making a compound of Formula VIII, or salt thereof, is described in for example U.S. Pat. No. 8,063,050 and WO 2013/173779. (The entire contents of U.S. Pat. No. 8,063,050, WO 2013/173784, and WO 2013/17379 are incorporated herein by reference for all relevant and consistent purposes.)

C. Reaction Products and Intermediate Compounds

It is to be noted that the present disclosure is still further directed to one or more of the nitrile-substituted reaction product or reaction intermediate compounds, or salts thereof, prepared by the processes illustrated herein, including for example the compounds of Formulae V$_b$, V$_c$, IV$_b$, and/or III, or salts thereof, as defined herein above.

D. Definitions

With respect to the present disclosure, the following terms have the meanings set forth below.

"Acyl" means a carbonyl containing substituent represented by the formula —C(O)—R in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are independently optionally substituted and as defined herein. Acyl groups include alkanoyl (e.g., acetyl), aroyl (e.g., benzoyl), and heteroaroyl (e.g., pyridinoyl).

The term "alkyl" as used herein refers to a saturated linear or branched-chain monovalent hydrocarbon radical of one to twelve carbon atoms, and in another embodiment one to six carbon atoms, wherein the alkyl radical may be optionally substituted independently with one or more substituents described herein. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (iPr, i-propyl, —CH(CH$_3$)$_2$), 1-butyl (n-Bu, n-butyl, —CH$_2$CH$_2$CH$_2$CH$_3$), 2-methyl-1-propyl (i-Bu, ibutyl, —CH$_2$CH(CH$_3$)$_2$), 2-butyl (s-Bu, s-butyl, —CH(CH$_3$)CH$_2$CH$_3$), 2-methyl-2-propyl (t-Bu, tbutyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (CH(CH$_3$)CH(CH$_3$)$_2$), 3-methyl-1-butyl (—CH$_2$CH$_2$CH(CH$_3$)$_2$), 2-methyl-1-butyl (CH$_2$CH(CH$_3$)CH$_2$CH$_3$), 1-hexyl (—CH$_2$CH$_2$CH$_2$CH$_2$CH$_2$CH$_3$), 2-hexyl (CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (CH(CH$_3$)CH$_2$CH(CH$_3$)$_2$), 3-methyl-3-pentyl (—C(CH$_3$)(CH$_2$CH$_3$)$_2$), 2-methyl-3-pentyl (CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (CH(CH$_3$)C(CH$_3$)$_2$), 1-heptyl, 1-octyl, and the like.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms, and in another embodiment two to six carbon atoms, with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), 1-propenyl, 1-buten-1-yl, 1-buten-2-yl, and the like.

The term "alkynyl" as used herein refers to a linear or branched monovalent hydrocarbon radical of two to twelve carbon atoms, and in another embodiment two to six carbon atoms, with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$C≡CH).

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

"Amino" means primary (i.e., —NH$_2$), secondary (i.e., —NRH), tertiary (i.e., —NRR) and quaternary (i.e., —N$^+$RRRX$^-$) amines, that are optionally substituted, in which R is independently alkyl, alkoxy, a cycloalkyl, a heterocyclyl, cycloalkyl, -substituted alkyl or heterocyclyl substituted alkyl wherein the alkyl, alkoxy, cycloalkyl and heterocyclyl are as defined herein. Particular secondary and tertiary amines are alkylamine, dialkylamine, arylamine, diarylamine, aralkylamine and diaralkylamine wherein the alkyls and aryls are as herein defined and independently optionally substituted. Particular secondary and tertiary amines are methylamine, ethylamine, propylamine, isopropylamine, phenylamine, benzylamine, dimethylamine, diethylamine, dipropylamine and diisopropylamine.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms, and in another embodiment three to eight carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, cyclohexenyl, cyclohexadienyl, cycloheptenyl, and the like. Bicyclic carbocycles include those having 7 to 12 ring atoms arranged, for example, as a bicyclo [4,5], [5,5], [5,6] or [6,6] system, or as bridged systems such as bicyclo[2.2.1]heptane, bicyclo[2.2.2]octane, and bicyclo [3.2.2]nonane. The cycloalkyl may be optionally substituted independently with one or more substituents described herein.

The term "aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring.

Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "heterocyclyl" and "heterocyclic ring" as used herein are used interchangeably and refer to a saturated or partially unsaturated carbocyclic radical of 3 to 12 membered ring atoms in which at least one ring atom is a heteroatom independently selected from nitrogen, oxygen and sulfur, the remaining ring atoms being C, where one or more ring atoms may be optionally substituted independently with one or more substituents described below. One embodiment includes heterocycles of 3 to 7 membered ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1, 1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

"Leaving group" refers to a portion of a first reactant in a chemical reaction that is displaced from the first reactant in the chemical reaction. Examples of leaving groups include, but are not limited to, hydrogen, halogen, hydroxyl groups, sulfhydryl groups, amino groups (for example —NRR, wherein R is independently alkyl, alkenyl, alkynyl, cycloalkyl, phenyl or heterocyclyl and R is independently optionally substituted), silyl groups (for example —SiRRR, wherein R is independently alkyl, alkenyl, alkynyl, cycloalkyl, phenyl or heterocyclyl and R is independently optionally substituted), —N(R)OR (wherein R is independently alkyl, alkenyl, alkynyl, cycloalkyl, phenyl or heterocyclyl and R is independently optionally substituted), alkoxy groups (for example —OR, wherein R is independently alkyl, alkenyl, alkynyl, cycloalkyl, phenyl or heterocyclyl and R is independently optionally substituted), thiol groups (for example —SR, wherein R is independently alkyl, alkenyl, alkynyl, cycloalkyl, phenyl or heterocyclyl and R is independently optionally substituted), sulfonyloxy groups (for example —OS(O)$_{1-2}$R, wherein R is independently alkyl, alkenyl, alkynyl, cycloalkyl, phenyl or heterocyclyl and R is independently optionally substituted), sulfamate groups (for example —OS(O)$_{1-2}$NRR, wherein R is independently alkyl, alkenyl, alkynyl, cycloalkyl, phenyl or heterocyclyl and R is independently optionally substituted), carbamate groups (for example —OC(O)$_2$NRR, wherein R is independently alkyl, alkenyl, alkynyl, cycloalkyl, phenyl or heterocyclyl and R is independently optionally substituted), and carbonate groups (for example —OC(O)$_2$RR, wherein R is independently alkyl, alkenyl, alkynyl, cycloalkyl, phenyl or heterocyclyl and R is independently optionally substituted). Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)). Other examples of leaving groups include substituted and unsubstituted amino groups, such as amino, alkylamino, dialkylamino, hydroxylamino, alkoxylamino, N-alkyl-N-alkoxyamino, acylamino, sulfonylamino, and the like.

"Amino-protecting group" as used herein refers to groups commonly employed to keep amino groups from reacting during reactions carried out on other functional groups. Examples of such protecting groups include carbamates, amides, alkyl and aryl groups, imines, as well as many N-heteroatom derivatives which can be removed to regenerate the desired amine group. Particular amino protecting groups are Ac (acetyl), trifluoroacetyl, phthalimide, Bn (benzyl), Tr (triphenylmethyl or trityl), benzylidenyl, p-toluenesulfonyl, Pmb (p-methoxybenzyl), Boc (tertbutyloxycarbonyl), Fmoc (9-fluorenylmethyloxycarbonyl) and Cbz (carbobenzyloxy). Further examples of these groups are found in: Wuts, P. G. M. and Greene, T. W. (2006) Frontmatter, in Greene's Protective Groups in Organic Synthesis, Fourth Edition, John Wiley & Sons, Inc., Hoboken, N.J., USA. The term "protected amino" refers to an amino group substituted with one of the above amino-protecting groups.

The term "substituted" as used herein means any of the above groups (e.g., alkyl, alkylene, alkenyl, alkynyl, cycloalkyl, aryl, heterocyclyl and heteroaryl) wherein at least one hydrogen atom is replaced with a substituent. In the case of an oxo substituent (=O) two hydrogen atoms are replaced. "Substituents" within the context of this invention include, but are not limited to, halogen, hydroxy, oxo, cyano, nitro, amino, alkylamino, dialkylamino, alkyl, alkenyl, alkynyl, cycloalkyl, alkoxy, substituted alkyl, thioalkyl, haloalkyl (including perhaloalkyl), hydroxyalkyl, aminoalkyl, substituted alkenyl, substituted alkynyl, substituted cycloalkyl, aryl, substituted aryl, heteroaryl, substituted heteroaryl, heterocycle, substituted heterocycle, —NR$^e$Rr, —NR$^e$C(=O)R$^f$, —NR$^e$C(=O)NR$^e$R$^f$, —NR$^e$C(=O)OR$^f$—NR$^e$SO$_2$Rr, —OR$^e$, —C(=O)R$^e$—C(=O)OR$^e$, —C(=O)NR$^e$R$^f$, —OC(=O)NR$^e$R$^f$, —SR$^e$, —SOR$^e$, —S(=O)$_2$R$^e$, —OS(=O)$_2$R$^e$, —S(=O)$_2$OR$^e$, wherein R$^e$ and R$^f$ are the same or different and independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycle, substituted heterocycle.

The term "halo" or "halogen" as used herein means fluoro, chloro, bromo or iodo.

The term "a" as used herein means one or more.

Reference to "about" a value or parameter herein includes (and describes) embodiments that are directed to that value or parameter per se and in one embodiment plus or minus 20% of the given value. For example, description referring to "about X" includes description of "X".

A "salt" of the various compounds and intermediates disclosed and prepared herein generally refer to essentially any salt form recognized by one of skill in the art to be suitable in the manufacture of the compounds and intermediates of the present disclosure. "Salt" as used herein is understood to encompass, but not be limited to, "pharmaceutically acceptable salts," and includes both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly organic non-toxic bases are isopropylamine, diethylamine, ethanolamine, tromethamine, dicyclohexylamine, choline, and caffeine.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

It is to be noted that the compounds detailed herein may contain one or more chiral centers. Accordingly, if desired, such compounds can be prepared or isolated as pure stereoisomers (such as individual enantiomers or diastereomers, or as stereoisomer-enriched mixtures). All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic or stereoisomer-enriched mixtures of such compounds can be separated using, for example, chiral column chromatography, chiral resolving agents, and the like.

It is to be further noted that all patents, patent applications, documents and articles cited herein are incorporated herein by reference in their entireties, for all relevant and consistent purposes.

While the processes and compounds of the present disclosure are described herein in conjunction with particular the enumerated embodiments, it is to be understood that they are not intended to limit the scope of the disclosure to these embodiments. On the contrary, the disclosure is intended to cover all alternatives, modifications, and equivalents. One skilled in the art will recognize many methods and materials similar or equivalent to those described herein, which could be used in the practice of the present process. Accordingly, the present disclosure is in no way limited to the methods and materials described herein.

Additionally, in the event that one or more of the incorporated literature and similar materials differs from or contradicts this disclosure, including but not limited to defined terms, term usage, described techniques, or the like, this disclosure controls.

EXAMPLES

The present disclosure can be further understood by reference to the following Examples, which provide details for the preparation of the various compounds illustrated in the Scheme 4, above.

Example 1: Malonate Conjugate Addition

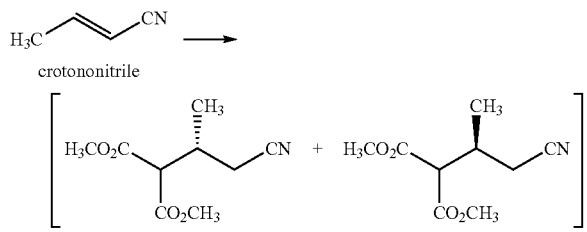

Dimethyl-2-(1-cyanopropan-2-yl)malonate

Sodium tert-pentoxide (65.7 g) was added to THF (900 g) and the mixture was stirred for 30 minutes (mins). Dimethylmalonate (433 g) was added and then the mixture was heated to 60-70° C. Crotononitrile (200 g) was added, while maintaining the internal temperature at 60-70° C. The mixture was stirred until reaction completion and then cooled to room temperature. Hydrochloric acid (HCl) in methanol (MeOH) was added until the mixture reached a pH of between 7-8, and then it was filtered. The filter cake was rinsed with THF (360 g). The collected solution or filtrate was distilled to remove volatiles and afforded crude dimethyl-2-(1-cyanopropan-2-yl)malonate as a colorless to light yellow oil that was used directly in the next step. $^1$H NMR (500 MHz, DMSO-d$_6$) δ 3.67 (s, 6H), 3.51 (d, 1H, J=7.5 Hz), 2.68 (dd, 1H, J=5, 17 Hz), 2.54 (dd, 1H, J=8, 17 Hz), 2.44 (m, 1H), 1.04 (d, 3H, J=7 Hz).

Example 2: Enzymatic Resolution

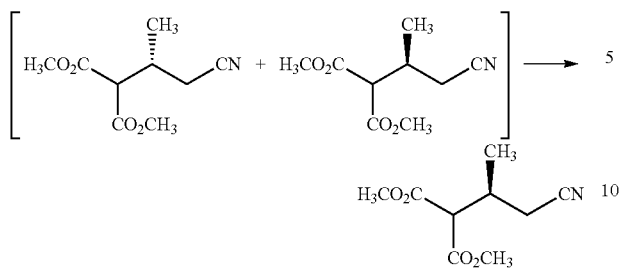

Exemplary enzymatic resolutions were carried out as further detailed below.

Example 2a—Dimethyl-(R)-2-(1-cyanopropan-2-yl) malonate via Nitrilase

A 1500 mL four-necked round-bottom flask equipped with a KPG stirrer, a thermometer and a dropping funnel was charged with 69.7 g (400 mmol) potassium sulfate and 5.44 g (40 mmol) potassium dihydrogenphosphate in 800 mL deionized water (pH 4.85). Sodium hydroxide (3.87 g, 32% aq solution) was added dropwise under stirring to a final pH of 7.2, and then the solution was stirred for 15 mins. Dimethyl 2-(1-cyanopropan-2-yl) malonate (199.5 g, 1.00 mol, 98% w/w) was added and then the biphasic emulsion was stirred for 5 mins. at 20-25° C. (pH remaining unchanged).

The enantioselective hydrolysis was started by the addition of 39 mL nitrilase solution Nit-BX4-56-H6 (c-Lecta, Leipzig, Germany, catalogue no. 10906-3L; 500 U/mL) within 5 mins. The addition funnel was rinsed with 8 mL deionized water, and the reaction mixture (pH 7.18) was stirred at 20-25° C. When the enantiomeric excess of the retained, and desired, nitrile reached 99.7% ee (after approx. 55% conversion; E approx. 50; after 43 hr; pH 6.93), the pH of the reaction mixture was adjusted to 2.0 by the dropwise addition of approx. 96 g 25% hydrochloric acid (temp. less than 28° C.; heavy precipitation of protein). The emulsion/suspension was stirred for 10 mins. and then readjusted to pH 7.5 by adding approx. 85 g of 32% sodium hydroxide solution (temp. less than 35° C.). The mixture was stirred for 10 mins., and then 500 mL ethyl acetate was added and the suspension/emulsion was stirred for another 5 min. The two phases were allowed to separate (approx. 3 mins.; protein precipitate largely in the organic phase), and then were consecutively filtered over a filter cloth (9 cm, 20 um). The filter was rinsed with 500 mL ethyl acetate, the organic phases in the filtrate combined, and then allowed to separate from the aqueous phase. The latter was extracted again with 1 L ethyl acetate. The combined organic phases were consecutively washed with 200 mL of 1 M sodium bicarbonate and 100 mL deionized water, respectively, and evaporated to dryness at 50° C./40 mbar/1.5 hr. to give 90.7 g (45%) of dimethyl-(R)-2-(1-cyanopropan-2-yl)malonate as a light yellow oil: $^1$H NMR (500 MHz, DMSO-$d_6$) δ 3.67 (s, 6H), 3.51 (d, 1H, J=7.5 Hz), 2.68 (dd, 1H, J=5, 17 Hz), 2.54 (dd, 1H, J=8, 17 Hz), 2.44 (m, 1H), 1.04 (d, 3H, J=7 Hz); $^{13}$C NMR (125 MHz, DMSO-$d_6$) δ 168.43, 119.30, 55.36, 53.00, 52.95, 30.41, 21.89, 17.17; $[\alpha]_{436}^{20}$ −2.2 (c=1, MeOH); HRMS calc'd. for $C_{19}H_{12}NO_4$ [M−H]$^-$: 198.0772. found: 198.0770. Analytics: 95.3% GC (trimethylsilylated with BSTFA); 99.7% ee (GC on BGB-175; 30 m×0.25 mm, 0.25 um; H2; 135 kPa; 90° C. to 150° C. with 2° C./min, to 180° C. with 20° C./min; inj. 200° C.; det. 250° C.; inj. vol. 1 ml; split 15:1; 30.77 min (R)-1, 31.09 min (S)-1; containing 2.5% ethyl acetate and <0.1% water).

Example 2b—Dimethyl-(R)-2-(1-cyanopropan-2-yl) malonate via Ester Hydrolysis Using Lipase CRL3

Dimethyl 2-(1-cyanopropan-2-yl) malonate (3.0 g, 15.1 mmol) was placed into reactor followed by the addition of 21 mL 0.03 M acetate buffer pH 5.2, 1.96 g potassium sulfate and 6.0 mL heptane. After 5 minutes stirring the addition of 60.0 mg cholesterol esterase from Candida cyclindracea [Roche, lot 10347322] (s/e 50) started the ester hydrolysis at room temperature (approx. 23° C.). The pH kept constant by the addition of 1.0 N sodium hydroxide solution consuming 7.6 mL (7.6 mmol) during 50 h stirring. Ethyl acetate (30 mL) was added subsequently and the reaction mixture was vigorously stirred 15 min forming an emulsion. 1.5 g filtration aid (Dicalite®) was added subsequently and the reaction mixture was vigorously stirred for further 15 min. before filtration through a filter-aid bed (Dicalite®). The two phases were separated. The aqueous phase was extracted additionally twice with ethyl acetate (50 mL). The organic phases were combined and washed three times with 50 mL 100 mM potassium phosphate buffer pH 7.2. The organic phase was dried over magnesium sulfate, filtered and evaporated obtaining 1.26 g (R)-dimethyl 2-(1-cyanopropan-2-yl) malonate (99.6% purity; 42% yield) as a colorless oil. Enantiomeric excess=100% ee (HPLC-method: column: Chiralpak IA-3 150 mm*4.6 mm, 3 μm; isocratic A: 95% heptane+0.10% TFA B: 5% ethanol; flow 2 ml/min; 30° C.; 214 nm; 130 bar; retention times: (S)-nitrile 3.4 min, (R)-nitrile 3.89 min).

Example 2c—Dimethyl-(R)-2-(1-cyanopropan-2-yl) malonate via Ester Hydrolysis Using Lipase EL030 (III)

Dimethyl 2-(1-cyanopropan-2-yl) malonate (300 mg, 1.51 mmol) was placed into a reactor followed by the addition of 29.7 mL 0.03 M MES buffer (pH 6.2) and 300 mg β-cyclodextrin. After 5 mins. stirring, the addition of 60.0 mg EL030 (III) [EUCODIS, lot 04804012SS0911] (s/e 5) started the ester hydrolysis at room temperature (approx. 23° C.). The pH was kept constant by the addition of 1.0 N sodium hydroxide solution, consuming 1.05 mL (1.05 mmol) during 48 hr stirring. Chiral HPLC analysis determined an enantiomeric excess=100% ee dimethyl-(R)-2-(1-cyanopropan-2-yl) malonate.

Example 2d—Dimethyl-(R)-2-(1-cyanopropan-2-yl) malonate via Nitrilase at pH 9

A 350 mL four-necked round-bottom flask equipped with a KPG stirrer, a thermometer and a dropping funnel was charged with 17.5 g (100 mmol) potassium sulfate, 1.36 g (10 mmol) potassium dihydrogenphosphate and 1.325 g sodium carbonate (12.5 mmol) in 200 mL deionized water (pH 9.2) and the solution stirred for 15 min. Dimethyl 2-(1-cyanopropan-2-yl) malonate (50.0 g, 250 mmol, 98% w/w) was added over 5 min and then the biphasic emulsion was stirred for 5 mins. at 20-25° C.

The enantioselective hydrolysis was started by the addition of 9.75 mL (4875 U) nitrilase solution Nit-BX4-56-H6 (c-Lecta, Leipzig, Germany, catalogue no. 10906-3L; 500 U/mL) within 2 mins. The addition funnel was rinsed with 2 mL deionized water, and the reaction mixture was stirred at 20-25° C. When the enantiomeric excess of the retained, and desired, nitrile reached 99% ee (after approx. 53% conversion; E approx. 80; after 18 hr; pH 8.2), the pH of the reaction mixture was adjusted to 2.0 by the dropwise addition of approx. 24.7 g 25% hydrochloric acid (temp. less than 27° C.; heavy precipitation of protein). The emulsion/suspension was stirred for 10 mins. and then readjusted to pH 7.5 by adding approx. 23.1 g of 32% sodium hydroxide solution (temp. less than 35° C.). The mixture was stirred for 10 mins., and then 125 mL ethyl acetate was added and the suspension/emulsion was stirred for another 5 min. The two phases were allowed to separate (approx. 3 mins.; protein precipitate largely in the organic phase), and then were consecutively filtered over a filter cloth (3 cm, 20 um). The filter was rinsed with 125 mL ethyl acetate, the organic phases in the filtrate combined, and then allowed to separate from the aqueous phase. The latter was extracted again with 250 mL ethyl acetate. The combined organic phases were consecutively washed with 50 mL of 1 M sodium bicarbonate and 25 mL deionized water, respectively, and evaporated to dryness at 50° C./40 mbar/1.5 hr. to give 23.1 g (46.2%) of dimethyl-(R)-2-(1-cyanopropan-2-yl)malonate as a light yellow oil in 99% ee and 94.9% GC (cf. Example 2a).

Example 2e—Dimethyl-(R)-2-(1-Cyanopropan-2-Yl)Malonate Via Nitrilase at pH 9

To a 350 mL four-necked round-bottom flask equipped with a KPG stirrer, a thermometer and a dropping funnel containing 50.0 g dimethyl 2-(1-cyanopropan-2-yl) malonate (250 mmol, 98% w/w) was added a solution of 7.62 g (20 mmol) disodium tetraborate decahydrate and 17.5 g (100 mmol) potassium sulfate in 200 mL deionized water (pH 9.3), and the biphasic emulsion was stirred for 10 mins. at 20-25° C.

The enantioselective hydrolysis was started by the addition of 9.75 mL (4875 U) nitrilase solution Nit-BX4-56-H6 (c-Lecta, Leipzig, Germany, catalogue no. 10906-3L; 500 U/mL) within 2 mins. The addition funnel was rinsed with 2 mL deionized water, and the reaction mixture was stirred at 20-25° C. When the enantiomeric excess of the retained, and desired, nitrile reached 99.8% ee (after 18 hr; pH 8.4), the pH of the reaction mixture was adjusted to 2.0 by the dropwise addition of approx. 27.7 g 25% hydrochloric acid (temp. less than 27° C.; heavy precipitation of protein). The emulsion/suspension was stirred for 10 mins. and then readjusted to pH 8.0 by adding approx. 25.3 g of 32% sodium hydroxide solution (temp. less than 32° C.). The mixture was stirred for 10 mins., and then 125 mL methyl tert.butyl ether was added and the suspension/emulsion stirred for another 5 mins. and then filtered over a filter cloth (5 cm, 20 um). The reaction vessel and the filter were rinsed with another 125 mL methyl tert.butyl ether, the organic phases in the filtrate combined, and then allowed to separate from the aqueous phase. The latter was extracted again with 250 mL methyl tert.butyl ether. The combined organic phases were consecutively washed with 50 mL of 1 M sodium bicarbonate and 25 mL deionized water, respectively, and evaporated to dryness at 50° C./7 mbar/2 hr. to give 21.32 g (42.2%) of dimethyl-(R)-2-(1-cyanopropan-2-yl)malonate as a light yellow oil in >99% ee and 95.7% GC (cf. Example 2a).

Example 3: Pyrimidine Synthesis

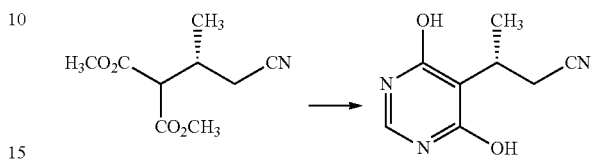

(R)-3-(4,6-Dihydroxypyrimidin-5-yl)butanenitrile. A reactor was charged with formamidine acetate (2.9 g) and MeOH (13.0 mL, 2.6 mL/g). The mixture was cooled to 5° C. under $N_2$, and then NaOMe (17.0 mL) was charged to the reactor, resulting in a slight exotherm. After cooling back to 5° C., a solution of dimethyl (R)-2-(1-cyanopropan-2-yl)malonate (5.0 g) in MeOH (3.0 mL) was added slowly to the above suspension, then the reaction mixture was warmed to 25° C. Stirring was continued for approx. 2 hrs, and then water (15.0 mL) was added and the pH was adjusted to 5-7 by portion-wise addition of concentrated HCl (4.1 mL) while keeping the temperature below 30° C. The reaction mixture was concentrated under vacuum to approximately ⅓ of the starting volume, and then sampled for MeOH content. Once MeOH was 10-20%, the slurry was cooled to 5° C. and the pH was adjusted to 4-6 by addition of concentrated HCl (1.25 mL, 0.25 mL/g). After stirring for 1 hr at 5° C., the resulting solids were collected by filtration. The filter cake was washed with cold water (15.0 mL, 3.0 vol, 5° C.) and dried in a vacuum oven at 70° C. overnight to give (R)-3-(4,6-dihydroxypyrimidin-5-yl)butanenitrile as an off-white solid (3.86 g, 86% yield): $^1$H NMR (500 MHz, DMSO-$d_6$) δ 11.85 (bs, 2H), 7.96 (s, 1H), 3.27 (m, 1H), 2.90 (dd, 1H, J=9, 17 Hz), 2.74 (dd, 1H, J=7, 17 Hz), 1.17 (d, 1H, J=7 Hz), $^{13}$C NMR (125 MHz, DMSO-$d_6$) δ 164.15, 148.16, 120.62, 103.17, 26.86, 21.07, 18.00; $[\alpha]_{436}^{20}$ −69.9 (c=1, N,N-dimethylacetamide); HRMS calc'd. for $C_8H_8N_3O_2$ [M−H]$^-$:178.0622. found: 178.0622.

Example 4: Chlorination-Bromination-$S_N$Ar Through-Process

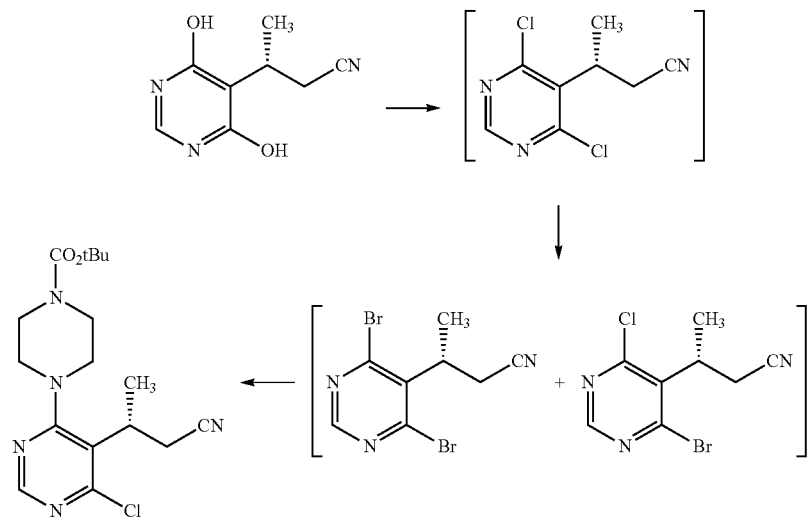

tert-Butyl (R)-4-(6-bromo-5-(1-cyanopropan-2-yl) pyrimidin-4-yl)-piperazine-1-carboxylate A reactor equipped with a reflux condenser was charged with (R)-3-(4,6-dihydroxypyrimidin-5-yl)butanenitrile (60.0 g, 334.9 mmol, 1 eq.), toluene (720 mL, 12 vol.) and 2,6-lutidine (39.0 mL, 1.0 eq.) at room temperature under $N_2$ atmosphere. The mixture was heated to 110° C. and $POCl_3$ (93.4 mL, 3 eq.) was slowly added, while maintaining the temperature at 105-115° C. After 2 hrs, the starting material was consumed completely as detected by HPLC (>99%). The biphasic reaction mixture was cooled to 10-20° C. internal temperature. To a separate reactor was added 0.4M $K_3PO_4$ pH 7 buffer (300 mL, 5 vol.) at room temperature under $N_2$ atmosphere. The chlorination reaction mixture was slowly added to the buffer solution while keeping the temperature at less than 30° C. Additionally, the pH of the quench mixture was maintained at 5-7 using 50% aq. NaOH (266 g, 4.4 wt.). Once the quench was complete, the layers were separated and the aqueous layer was extracted with toluene (300 mL, 5 vol.). The combined organic phases were washed with 0.2 N aqueous HCl (250 mL, 4.2 vol). The organic solution was washed with water (2×200 mL). The resulting solution was distilled under vacuum until the toluene level in the crude product was less than 20 wt % as determined by GC analysis. An analytical sample was obtained by chromatography of a concentrated sample on silica gel using EtOAc/hexanes (1:1) as eluent. (R)-3-(4,6-dichloropyrimidin-5-yl)butanenitrile: $^1$H NMR (500 MHz, DMSO-$d_6$) δ 8.83 (s, 1H), 3.93 (m, 1H), 3.11 (m, 2H), 1.43 (d, 3H, J=7 Hz); $^{13}$C NMR (125 MHz, DMSO-$d_6$) δ 161.40, 157.05, 133.07, 119.25, 32.57, 20.84, 16.80; $[\alpha]_{436}^{20}$+16.8 (c=1, MeOH); HRMS calc'd. for $C_8H_8Cl_2N_3$ $[M+H]^+$: 216.0092. found: 216.0092.

To the crude product was added acetonitrile (216.0 mL, 3.6 V). The nitrogen line was configured so that it flowed over the reactor headspace and exited after the distillation head. The reaction mixture was then heated to 70-80° C. (target=75° C.) to produce a yellow solution. Bromotrimethylsilane (90 mL, 1.5 V, 200 mol %) was then added at 75° C. over 10 mins. This caused the reaction temperature to drop by approx. 2-5° C. and distillation slowly began. After stirring at 75° C. for 30 mins., additional bromotrimethylsilane (66 mL, 1.1 V, 150 mol %) was added over 90 mins. at 75° C. This solution was allowed to stir at temperature for a total of 16-18 hr, and then a sample was pulled and analyzed by HPLC for conversion. (If incomplete, additional bromotrimethylsilane is added in 0.25 eq. increments, until the desired level is attained.) An analytical sample was obtained by chromatography of a concentrated sample on silica gel using EtOAc/hexanes (1:1) as eluent. (R)-3-(4,6-dibromopyrimidin-5-yl)butanenitrile: $^1$H NMR (500 MHz, DMSO-$d_6$) δ 8.68 (s, 1H), 3.97 (m, 1H), 3.23 (dd, 1H, J=9, 17 Hz), 3.13 (dd, 1H, J=8, 17 Hz), 1.44 (d, 3H, J=7 Hz); $^{13}$C NMR (125 MHz, DMSO-$d_6$) δ 157.04, 137.23, 119.13, 36.00, 20.77, 16.73; $[\alpha]_{436}^{20}$+39.5 (c=1, MeOH); HRMS calc'd. for $C_8H_8Br_2N_3$ $[M+H]^+$: 303.9079. found: 303.9087.

The reaction mixture was cooled to 20-25° C. internal temperature and diluted with acetonitrile (sufficient amount to obtain 0.5 M solution). Triethylamine (93.6 mL, 1.56 V, 200 mol %) and water (36.0 mL, 0.60 V) were then slowly added to the reaction and a sample was taken for pH measurement (1:100 dilution into water). If the pH is greater than 10, N-BOC-piperazine (71.5 g, 1.19 W, 115 mol %) is added and stirring continued at 20-25° C. If the pH is less than 10, triethylamine is added until the desired pH is reached. The reaction was stirred at 20-25° C. for 16-18 hrs.

A sample was pulled and analyzed by HPLC for conversion (G02855614 ≤2%). If no solids are present, tert-butyl (R)-4-(6-bromo-5-(1-cyanopropan-2-yl)pyrimidin-4-yl)piperazine-1-carboxylate (6.9 g, 0.12 wt) is used to seed. Water (720.0 mL, 18.0 V) was slowly added to precipitate the product. The mixture was cooled to 5° C. and stirred for at least 2 h and then filtered. The filter cake was washed with room temperature water (360.0 mL, 6.0 V) and then placed in a vacuum oven at 70-80° C., until a constant weight of off-white to white powder was obtained (123 g, 90% yield) of tert-butyl (R)-4-(6-bromo-5-(1-cyanopropan-2-yl)pyrimidin-4-yl)piperazine-1-carboxylate: $^1$H NMR (500 MHz, DMSO-$d_6$) δ 8.41 (s, 1H), 3.41 (bm, 4H), 3.24 (bm, 4H), 3.08 (m, 2H), 1.48 (d, 3H, J=7 Hz), 1.41 (s, 9H); $^{13}$C NMR (125 MHz, DMSO-$d_6$) δ 168.23, 155.67, 154.44, 152.15, 125.08, 119.51, 79.62, 50.27, 31.37, 28.52, 21.64, 17.66; $[\alpha]_{435}^{20}$+78.9 (c=0.3, MeOH); HRMS calc'd. for $C_{17}H_{25}BrN_5O_2$ $[M+H]^+$: 410.1186. found: 410.1180.

Example 5: Grignard Cyclization

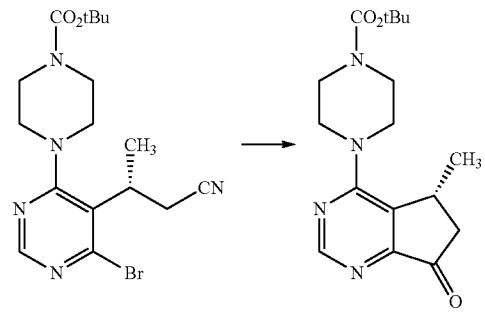 [SMILES: C[C@H](CC#N)c1c(Br)ncnc1N1CCN(C(=O)OC(C)(C)C)CC1 ; C[C@@H]1CC(=O)c2ncnc(N3CCN(C(=O)OC(C)(C)C)CC3)c21]

tert-Butyl (R)-4-(5-methyl-7-oxo-6,7-dihydro-5H-cyclopenta[d]pyrimidin-4-yl)piperazine-1-carboxylate A solution of tert-butyl (R)-4-(6-bromo-5-(1-cyanopropan-2-yl)pyrimidin-4-yl)piperazine-1-carboxylate (2.00 g) in anhydrous 2-MeTHF (5.00 mL) and anhydrous toluene (5.00 mL) was cooled to 5° C. in a 50 mL vessel. A solution of iPrMgCl (3.52 mL, 105 mol %, 1.45 M in THF) was added over 4 hrs via a syringe pump while maintaining the batch temperature at 5±3° C. The orange-brown reaction mixture was quenched into aqueous $NaHSO_4$ solution over 5 mins., while maintaining the batch temperature at 20±5° C. The pH value of the aqueous layer was measured to be approx. 5 by pH paper. The mixture was stirred for 30 mins. at 20±5° C. and the layers were separated. The organic layer was concentrated under vacuum ($T_j$=35° C., 100 mbar) until the solution concentration was 190-210 mg/g. The solution was then seeded with tert-butyl (R)-4-(5-methyl-7-oxo-6,7-dihydro-5H-cyclopenta[d]pyrimidin-4-yl)piperazine-1-carboxylate (0.10 g, 0.05 g/g) and stirred for 1 hr at 20-25° C. Degassed heptane (14.0 mL, 7.0 mL/g) was added over 2 hrs, and then the solution was filtered and washed with room temperature heptane/toluene (80:20, 6.0 mL, 3.0 mL/g) and dried in a vacuum oven at 60° C., until a constant weight of tan-orange powder was obtained. The dried, crude ketone (1.25 g, 1.0 wt), 2-propanol (5.00 mL, 4.0 mL/g) and water (1.25 mL, 1.0 mL/g) were charged to a 50 mL vessel. The slurry was degassed with $N_2$ for at least 10 mins., then heated to 40° C. until all solids were dissolved. This solution was then cooled to 25° C. and seeded (0.06 g, 0.05 g/g) and stirred for at least 1 hr. The slurry was cooled to −5° C. over 1 hr, then degassed water (6.04 mL, 4.83 mL/g) was added over 1 hr. This slurry was allowed to stir overnight, then filtered and washed with a degassed, pre-chilled (−5° C.) mixture of 2-propanol (1.5 mL, 1.2 mL/g) and water (3.5 mL, 2.8 mL/g). The solids were dried in a vacuum oven at 70° C. until a constant weight of tan-orange powder was obtained. The overall yield for process was approximately 68-73% (1.1 g): $^1$H NMR (500 MHz, DMSO-$d_6$) δ 8.60 (s, 1H), 3.82 (m, 2H), 3.72 (m, 1H), 3.65 (m, 2H), 3.50 (m, 2H), 3.42 (m, 2H), 2.90 (dd, 1H, J=7, 19 Hz), 2.25 (dd, 1H, J=2, 19 Hz), 1.41 (s, 9H), 1.19 (d, 3H, J=7 Hz); $^{13}$C NMR (125 MHz, DMSO-$d_6$) δ 205.75, 161.96, 158.89, 157.97, 154.34, 137.39, 79.67, 45.77, 43.39, 43.25, 31.22, 28.52, 20.40; $[\alpha]_{436}^{20}$+453.7 (c=1, MeOH); HRMS calc'd. for $C_{17}H_{24}N_4O_3$ [M+H]$^+$: 333.1921. found: 333.1916.

Example 6: Comparative Example—Attempted Grignard

Cyclization of Chloro-Nitrile Substituted Analogue Compound

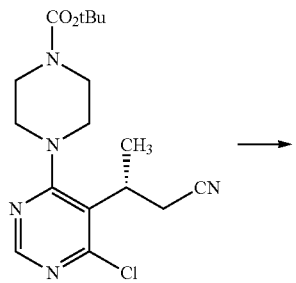 [SMILES: C[C@H](CC#N)c1c(Cl)ncnc1N1CCN(C(=O)OC(C)(C)C)CC1]

Initially, the cyclization of a chloropyrimidine compound was attempted using transition metal catalysis (e.g., Pd, Rh, Ir) with a variety of phosphine ligands. The des-chloropyrimidine was consistently found to be the main product from the reaction.

Attempts at cyclizing the corresponding chloropyrimidine-nitrile, such as those further detailed below, to the ketone were made using a variety of transition metal pre-catalysts, including Ir, Ni, Pd, Rh and Ru. These pre-catalysts were complexed with a range of mono and bidendate phosphine ligands prior to the start of the reactions. The use of additives, such as Lewis and Bronsted acids, water, transition and phase transfer catalysts were also tested. Reducing agents ranged from inorganic metals, such as zinc, to organic reducing agents, like formate salts. Lastly, a diverse set of solvents were investigated, including water-miscible ethers, alcohols, polar aprotic to non-polar hydrocarbons and carbonates. In all of these cases, the highest yield obtained from the screening experiments was approximately 20% of the desired ketone product, with the remainder being starting material degradation products. The major byproduct formed in many of these reactions was the des-chloro reduction product.

Example 6a: tert-butyl 4-(5-methyl-7-oxo-5,6-dihydrocyclopenta [d]pyrimidin-4-yl)piperazine-1-carboxylate A slurry of Pd(OAc)$_2$ (6.1 mg, 0.10 equiv.), dimethylphenylphosphine (15.1 mg, 0.40 equiv.) and 1,2-dichloroethane (2.0 mL, 20.0 mL/g) was stirred at 20-25° C. for 15 mins., then the solvent was removed in vacuo. Zinc powder (35.7 mg, 2.0 equiv.), tert-butyl 4-[6-chloro-5-(2-cyano-1-methyl-ethyl)pyrimidin-4-yl]piperazine-1-carboxylate (100.0 mg, 1.0 equiv.) and DMF (6.0 mL, 60.0 mL/g) were added and the slurry was heated at 110° C. for 18 hrs. The assay yield of the crude reaction mixture was 15.8% (14.4 mg).

Example 6b: tert-butyl 4-(5-methyl-7-oxo-5,6-dihydrocyclopenta [d]pyrimidin-4-yl)piperazine-1-carboxylate A slurry of NiCl$_2$(DME) (24.0 mg, 0.40 equiv.), dimethylphenylphosphine (15.1 mg, 0.40 equiv.) and 1,2-dichloroethane (2.0 mL, 20.0 mL/g) was stirred at 20-25° C. for 15 mins., then the solvent was removed in vacuo. Zinc powder (35.7 mg, 2.0 equiv.), tert-butyl 4-[6-chloro-5-(2-cyano-1-methyl-ethyl)pyrimidin-4-yl]piperazine-1-carboxylate (100.0 mg, 1.0 equiv.) and DMF (6.0 mL, 60.0 mL/g) were added and the slurry was heated at 110° C. for 18 hrs. The LC assay yield of the crude reaction mixture was 14.5% (13.2 mg).

Example 6c: tert-butyl 4-(5-methyl-7-oxo-5,6-dihydrocyclopenta [d]pyrimidin-4-yl)piperazine-1-carboxylate A slurry of NiCl$_2$(DME) (24.0 mg, 0.40 equiv.), dimethylphenylphosphine (15.1 mg, 0.40 equiv.) and 1,2-dichloroethane (2.0 mL, 20.0 mL/g) was stirred at 20-25° C. for 15 mins., then the solvent was removed in vacuo. Zinc powder (35.7 mg, 2.0 equiv.), tert-butyl 4-[6-chloro-5-(2-cyano-1-methyl-ethyl)pyrimidin-4-yl]piperazine-1-carboxylate (100.0 mg, 1.0 equiv.), Mg(OEt)$_2$ (13.2 mg, 0.40 equiv.) and DMF (6.0 mL, 60.0 mL/g) were added and the slurry was heated at 110° C. for 18 hrs. The LC assay yield of the crude reaction mixture was 19.0% (17.3 mg).

Example 7: Comparative Example

Attempted Bromination Reaction Using HBr

Attempted bromination of the dichloropyrimidine nitrile with excess HBr and acetic acid or sodium bromide, and activation with methanesulfonic acid or copper catalysis, in a variety of solvents failed to afford useful amounts of the corresponding dibromopyrimidine nitrile.

For example, bromination of dichloropyrimidine nitrile using excess HBr in acetic acid or NaBr with stoichiometric methanesulfonic acid in acetonitrile gave only incomplete conversion to the desired dibromopyrimidine with evidence of reversibility and product decomposition based on HPLC analysis of the reaction mixtures. Alternatively, reaction of dichloropyrimidine nitrile with excess sodium bromide and 5 mol % CuI as catalyst and 10 mol % N,N'-dimethylethylenediamine or 4,4'-di-tert-butyl-2,2'-bipyridine as ligands in acetonitrile, dioxane or 1-butanol at 80-120° C. showed either no desired product or competing addition of the solvent or diamine ligand to the pyrimidine ring.

Additionally, it is to be understood that particular numerical values recited herein, including for example reagent concentrations or ratios, reaction times, reaction temperatures, and the like, are intended to disclose and encompass all values there between, as well as all ranges that may be created by the selection of any two values thereof. For example, reference to a reaction temperature of "about 20° C., 10° C., about 0° C., or less" is to be understood to encompass reaction temperature ranges of between about 0°

C. and about 20° C., between about 0° C. and about 10° C., between about 10° C. and about 20° C., or any two values there between.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

As used herein, reference to "a" or "an" means "one or more." Throughout, the plural and singular should be treated as interchangeable, other than the indication of number. For example, reference to "a compound" includes a single compound as well as one or more additional compounds, reference to "a pharmaceutically acceptable carrier" includes a single pharmaceutically acceptable carrier as well as one or more additional pharmaceutically acceptable carriers, and the like.

What is claimed is:

1. A process for preparing a compound of Formula I:

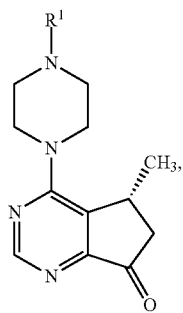

Formula I or a salt thereof, the process comprising:
(a) cyclizing a compound of VI$_b$:

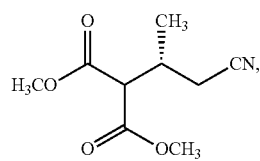

Formula VI$_b$ or a salt thereof to form a compound of Formula (V);

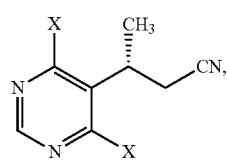

Formula V wherein each X is hydroxyl;
(b) brominating the compound of Formula V or a salt thereof with a brominating agent to form a compound of Formula IV:

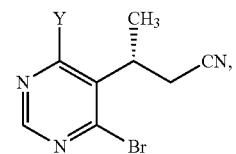

Formula IV or a salt thereof, wherein Y is bromo;
(c) contacting the compound of Formula IV with a piperazine compound having the structure:

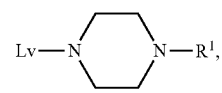

or a salt thereof, wherein Lv is a leaving group and R$^1$ is an amino protecting group to form a compound of Formula III:

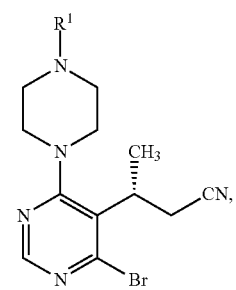

Formula III or a salt thereof; and
(d) contacting the compound of Formula III with a metalating agent to form the compound of Formula I, or a salt thereof; wherein R$^1$ is hydrogen or an amino protecting group.

2. The process of claim 1, wherein Lv is selected from hydrogen and a halogen, and R$^1$ is selected from acetyl, trifluoroacetyl, phthalimidyl, benzyl, triphenylmethyl, benzylidenyl, p-toluenesulfonyl, p-methoxybenzyl, tertbutyloxycarbonyl, 9-fluorenylmethyloxycarbonyl and carbobenzyloxy.

3. The process of claim 1, wherein the brominating agent is selected from bromine, bromotrimethylsilane, phosphorus oxybromide, N-bromosuccinimide, and phosphorus tribromide.

4. The process of claim 1, wherein distillation is used to remove volatile byproducts during the bromination reaction.

5. The process of claim 1, wherein the process comprises contacting the compound or a salt thereof of Formula VI$_b$ with a formamidine salt to cyclize the compound of Formula VI$_b$, or a salt thereof.

6. The process of claim 1, wherein R$^1$ is selected from acetyl, trifluoroacetyl, phthalimidyl, benzyl, triphenylmethyl, benzylidenyl, p-toluenesulfonyl, p-methoxybenzyl, tertbutyloxycarbonyl, 9-fluorenylmethyl oxycarbonyl and carbobenzyloxy.

7. The process of claim 1, wherein the metalating agent is an organometal compound.

8. The process of claim 7, wherein the organometal compound is selected from isopropylmagnesium chloride, isopropylmagnesium chloride lithium chloride complex, sec-butylmagnesium chloride, n-butyllithium, sec-butyllithium, t-butyllithium, lithium tri-n-butylmagnesiate, lithium triisopropylmagnesiate, and lithium (isopropyl)(di-n-butyl)magnesiate.

9. The process of claim 1, wherein $R^1$ is tertbutyloxycarbonyl.

10. The process of claim 1, wherein Lv is hydrogen.

11. The process of claim 1, wherein the metalating agent is an organomagnesium compound.

12. The process of claim 11, wherein the organomagnesium compound is a $C_1$-$C_6$ alkylmagnesium halide.

13. The process of claim 11, wherein the organomagnesium compound is isopropylmagnesium chloride or sec-butylmagnesium chloride.

14. The process of claim 11, wherein the organomagnesium compound is isopropylmagnesium chloride.

* * * * *